(12) United States Patent
Caldwell et al.

(10) Patent No.: US 6,670,199 B2
(45) Date of Patent: *Dec. 30, 2003

(54) COMPOSITION AND METHOD FOR REGULATING THE ADHESION OF CELLS AND BIOMOLECULES TO HYDROPHOBIC SURFACES

(75) Inventors: Karin D. Caldwell, Salt Lake City, UT (US); Patrick A. Tresco, Sandy, UT (US); Jennifer Neff, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/946,079

(22) Filed: Sep. 4, 2001

(65) Prior Publication Data

US 2002/0019037 A1 Feb. 14, 2002

Related U.S. Application Data

(60) Continuation of application No. 08/784,203, filed on Jan. 15, 1997, now Pat. No. 6,284,503, which is a continuation-in-part of application No. 08/399,913, filed on Mar. 7, 1995, now Pat. No. 5,728,588, which is a division of application No. 08/110,169, filed on Aug. 20, 1993, now Pat. No. 5,516,703.

(51) Int. Cl.[7] ................ G01N 33/547; G01N 33/569; C12N 11/08
(52) U.S. Cl. ................ 436/532; 435/7.21; 435/7.24; 435/29; 435/34; 435/40.5; 435/181; 436/531; 436/533; 436/811; 436/823; 530/391.1; 530/816
(58) Field of Search ................ 436/532, 531, 436/533, 823, 811; 530/391.1, 816; 435/181, 7.21, 7.24, 29, 34, 40.5

(56) References Cited

U.S. PATENT DOCUMENTS

| | | | |
|---|---|---|---|
| 3,966,580 A | 6/1976 | Janata et al. | 204/195 |
| 4,048,416 A | 9/1977 | Axen et al. | 526/9 |
| 4,149,003 A | 4/1979 | Carlsson et al. | 546/261 |
| 4,179,337 A | 12/1979 | Davis et al. | 435/181 |
| 4,259,474 A | 3/1981 | Chakrabarti et al. | 528/388 |
| 4,264,766 A | 4/1981 | Fischer | 536/51 |
| 4,330,677 A | 5/1982 | Linke et al. | 562/583 |
| 4,711,951 A | 12/1987 | Axen et al. | 530/323 |
| 4,929,510 A | 5/1990 | Ruckenstein et al. | 428/520 |
| 5,006,333 A | 4/1991 | Saifer et al. | 424/78 |
| 5,043,278 A | 8/1991 | Nagaoaka et al. | 435/181 |
| 5,219,926 A | 6/1993 | Lindman et al. | 525/54.1 |
| 5,248,820 A | 9/1993 | Murtiashaw | 562/538 |
| 5,405,618 A | 4/1995 | Buttery et al. | 424/486 |
| 5,516,703 A | 5/1996 | Caldwell et al. | 436/532 |
| 5,567,859 A | 10/1996 | Emanuele et al. | 568/624 |
| 5,728,588 A | 3/1998 | Caldwell et al. | 436/532 |
| 6,284,503 B1 | 9/2001 | Caldwell et al. | 435/181 |

FOREIGN PATENT DOCUMENTS

| | | |
|---|---|---|
| EP | 11237 | 5/1980 |
| EP | 98110 | 1/1984 |
| EP | 215456 | 3/1987 |
| WO | WO 89/01033 | 2/1989 |
| WO | WO 92/16555 | 10/1992 |
| WO | WO 95/06251 | 3/1995 |
| WO | WO 9604924 | 2/1996 |
| WO | WO 9615223 | 5/1996 |
| WO | WO 9616541 | 6/1996 |
| WO | PCT/US96/25921 | 8/1996 |

OTHER PUBLICATIONS

Li et al., "Chemical Modification of Surface Active Poly (ethylene oxide)—Poly (propylene oxide) Triblock Copolymers," Bioconjugate Chem., 1996 7, 592–99.

Kioukia et al., "Influence of Agitation and Sparging on the Growth Rate and Infection of Insect Cells in Bioreactors and a Comparison with Hybridoma Culture," Biotechnology Program, 1996, 12 (6) 779–785.

Johnston, "Absorption of Recombinant Human Granulocyte Colony Stimulating Factor (rhG–CSF) to Polyvinyl Chloride, Polypropylene, and Glass: Effect of Solvent Additives" Journal Of Pharmacy Science Technology, 1996, 50 (4) 238–245.

Topchieva, "Conjugates of Proteins with Block Polymers of Ethylene Oxide and Propylene Oxide," Chemistry Modif. Enzymes, 1996, 637–654.

Li et al., "Plasma Protein Interactions with Pluronic–Treated Colloids," Colloids Surf., 1996, 7 (1/2) 9–22.

Jansen et al., "Coadsorption of Steriods and Nonionic Surfactants on Polystyrene Latex Particles from Aqueous Solutions," Journal of Colloid Interface Science., 1996, 179 (2), 578–586.

Edwards, et al. "Effects of Pluronic F–68 (Poloxamer 188) on Platelet Aggregation in Human Whole Blood," Thromb. Res., 1996, 81 (4) 511–12.

Dewez et al., "Coupled Influence of Substratum Hydrophilicity and Surfactant on Epithelial Cell Adhesion", Journal of Biomedical Material Research, 1996, 30 (3) 373–78.

Efremova et al., "Conjugates of A–Chymotrypasin with Poly (alkylene oxides) in Hydrated Reversed Micelles", Biokhymiya, (Moscow), 1996, 61(1) 160–169.

Dewez et al., "Coupled Influence of Substratum Hydrophilicity and Surfactant on Epithelial Cell Adhesion", Journal of Miomedical Materials Res., 1996, 30 (3) 373–383.

(List continued on next page.)

Primary Examiner—Mary E. Ceperley
(74) Attorney, Agent, or Firm—Madson & Metcalf

(57) ABSTRACT

The present invention is directed to a composition and method for regulating the adhesion of cells and biomolecules to hydrophobic surfaces and hydrophobic coated surfaces. The composition is a biomolecule conjugated end-group activated polymer (EGAP). The biomolecule conjugated EGAP can be put to numerous uses including cell adhesion, cell growth, cell sorting, and other biological assays.

21 Claims, 9 Drawing Sheets

OTHER PUBLICATIONS

McPherson, et al., "Analysis of the Prevention of Protein Absorption by Steric Repulsion Theory", ACS Symp. Ser., 1995, 602 (Proteins at Interfaces 2), 395–404.

Lowe et al., "Enhanced Protoplast Growth at the Interface Between Oxygenated Fluorocarbon Liquid and Aqueous Culture Medium Supplemented with Pluronic F–68," Artificial Cells, Blood Substitutes, Immobilization Biotechnology, 1995, 23(3), 417–422.

Yan et al., "Calorimetric Observations of Protein Conformation at Solid–Liquid Interfaces", Protein Conformation at Solid–Liquid Interfaces, 1995, 257–268.

Topchieva et al., "Conjugates of Proteins with Block Co–Polymers of Ethylene and Propylene Oxides," Biotechnol., Genet. Eng. Rev., 1994, volume date 1994, 12, 357–382.

Armstrong et al., "Protein Absorption to Potential Drug Targeting System," Proc. Int. Symp. Controlled Release Bioact. Mater., 1994, $21^{st}$, 182–83.

Schroen et al., "Membrane Modification to Avoid Wettability Changes Due to Protein Adsorption in an Emulsion/Membrant Bioractor," Journal of Membrance Science, 80, 1993, 265–274.

Rudt et al., "In Vitro Phagocytosis Assay of Nano– and Microparticles by Chemiluminescence, II. Effect of Surface Modification by Coating of Particles with Poloxamer on the Phagocytic Uptake," Journal of Controlled Release, 25, 1993, pp. 51–59.

Zhang et al., "Effect of Pluronic F–68 on the Mechanical Properties of Mammalian Cells", Enzyme Microb. Technol. 1992, 14(12), 980–83.

Al–Rubeai, et al. "The Effect of Pluronic F–68 on Hybridoma Cells in Continuous Culture," Appl. Microbiol. Biotechnol., 1992, 37(1), 44–45.

Brinkley, "A Brief Survey of Methods for Preparing Protein Conjugates with Dyes, Haptens, and Cross–Linking Reagents," Bioconjugate Chem. 1992, 3, pp. 2–13.

Tiberg et al., "Immobilization of Protein to Surface–Grafted PEO/PPO Block Copolymers", Colloid & Polymer Science, 270m 1992, 1188–93.

Li et al.; "Size Analysis of a Block Copolymer–Coated Polystyrene Latex," American Chemical Society, 1991, Chapter 16, 246–262.

Schumpp et al., "Optimization of Culture Conditions for High Cell Density Proliferation of HL–60 Human Promyelocytic Leukemia Cells," Journal of Cell Science, 1990, 97 (4), 639–647.

Lee et al., "Protein–Resistant Surfaces Prepared by PEO–Containing Block Copolymer Surfactants," Journal of Biomedical Materials Research, vol. 23, 1989, 351–368.

Carlsson et al., "Protein Thiolation and Reversible Protein–Protein Conjugation," BioChem Journal 173, 1978, 723–737.

Kabakoff, "Chemical Aspects of Enzyme–Immunoassay," Enzyme–Immunoassay, Chapter 4, 71–105.

Li, Janq–Thun, "Plasma Protein Interactions with Copolymer–Stabilized Colloids," Disseration Abstracts International, vol. 54, No. 78, 3735 (1993).

Kirillova, G.P., et al. "The influence of Pluronics and Their Conjugates with Proteins on the Rate of Oxygen Consumption by Liver Mitochondria and Thymus Lymphocytes." Biotechnol., Appl. Biochem., vol. 18, No. 3 329–339 (1993).

COMPOSITION AND METHOD FOR REGULATING THE ADHESION OF CELLS AND BIOMOLECULES TO HYDROPHOBIC SURFACES

1. RELATED APPLICATIONS

This application is a continuation of application Ser. No. 08/784,203, filed Jan. 15, 1997, and entitled Composition and Method for Regulating the Adhesion of Cells and Biomolecules to Hydrophobic Surfaces, now U.S. Pat. No. 6,284,503, which is a continuation-in-part of U.S. patent application Ser. No. 08/399,913 filed Mar. 7, 1995, and entitled "Coating of Hydrophobic Surfaaces to Render Them Protein Resistant While Premitting Covalent Bonding," now U.S. Pat. No. 5,728,588, which is a divisional of appl. Ser. No. 08/110,169, filed Aug. 20, 1993, now U.S. Pat. No. 5,516,703 issued May 14, 1996 and entitled "Coating of Hydrophobic Surfaces To Render Them Protein Resistant While Permitting Covalent Attachment of Specific Ligands," which applications and patents are incorporated herein by reference.

2. FIELD OF THE INVENTION

The present invention is related to a composition and method for regulating the adhesion of cells, organisms, and molecules to hydrophobic surfaces. More specifically, the present invention is directed to a biomolecule, such as proteins, peptides amino acids, nucleic acids, lipids, and carbohydrates conjugated to end-group activated polymers (EGAPs) and uses thereof.

3. TECHNICAL BACKGROUND

Normal development and function in living organisms require interactions between cells and the molecules in the surrounding environment. One way cells communicate is via molecules that span the membrane of the cell called transmembrane proteins. When the portion of the transmembrane protein which is outside of the cell encounters specific molecules in the surrounding environment, it undergoes structural and conformational changes which triggers biological reactions inside the cell.

For example, in vivo, cells form complex multilayer structures which ultimately form tissues and organs. Tissue and organ formation, however, requires specific contacts with the environment. These cells are referred to as "anchorage-dependent" because they will not grow properly, if at all, unless they are anchored to others cells, an extracellular matrix (ECM), or other surface.

An ECM is a complex and variable array of molecules secreted by cells, such as collagens, glycosaminoglycans, proteoglycans, and glycoproteins. Together these cellular products form the basal lamina, bone, and cartilage which give tissues and organs their shape and strength. In fact, contact between anchorage-dependent cells and the ECM in many instances plays a dramatic role in determining the cells' shape, position, metabolism, differentiation and growth.

Cell contact is also important in other biological functions, such as the activation of an immune response. The immune system is a complex network of cells that have the ability to recognize and rid the body of foreign substances, such as viruses, bacteria and parasites. One mechanism used by the immune system to rid itself of foreign substances is a humoral response. A humoral response involves activation of specific cells called B cell lymphocytes. B-cells are activated when transmembrane proteins on their surface bind to foreign substances called antigens. Specifically, binding of B-cells to antigens stimulates B cells to proliferate and differentiate into immunoglobulin or antibody producing plasma cells.

The antibodies produced by plasma cells travel throughout the body binding to the pathogen or foreign substance. Binding of antibodies to foreign substances activates several other immunological pathways, including the "complement" pathway. The complement pathway is designed to destroy the foreign substance and to initiate an inflammatory response in the organism.

While cell contact with other cells and the environment is critical to the overall health and biological function of an organism, it creates unique problems in the art of biotechnology. Specifically, two areas where cell contact requirements create problems are: (1) cell culture; and (2) biomaterial transplantation.

Tissue or cell cultures comprise cells from a plant or animal which are grown outside the organism from which they originate. These cells are often grown, for example, in petri dishes under specific environmental conditions. Cell cultures are of great importance because they represent biological "factories" capable of producing large quantities of biological products such as growth factors, antibodies, and viruses. These products can then be isolated from the cell cultures and used, for example, to treat human disease. In addition, cell cultures are a potential source of tissue which could be used for transplantation into humans. For example, cell cultured skin cells could potentially be used in skin grafts to replace diseased or damaged skin. Finally, cell cultures usually comprise cells from only one or a few tissues or organs. Consequently, cell cultures provide scientists with a system for studying the properties of individual cell types without the complications and risk of working with the entire organism. For example, the effects of pharmaceutical drugs on certain cell types could be tested on cell cultures prior to clinical trials in order to assess the drug's health risks.

Like most cells in vivo, cells grown in culture are either anchored to an ECM or another cell. Only cells of the circulatory system (e.g., lymphocytes and red blood cells) grow unattached and suspended in solution in vitro. Many anchorage-dependent cells can grow on glass or plastic surfaces, such as polystyrene. These cells, however, often lose their natural architecture and do not function normally (e.g., the ability to differentiate and respond to hormones). Accordingly, these cells do not precisely mimic a cell's biological functions in vivo and thus have limited potential.

For this reason, glass and plastic cell culture dishes are often coated with an ECM protein such as collagen, fibronectin, laminin and the like. These proteins bind to surfaces such as polystyrene through a process known as adsorption. Although ECM coated cell culture surfaces have led to improved culture conditions, they are far from ideal.

First, biomolecules, such as proteins, often become inactivated upon adsorption to hydrophobic surfaces. The biological activity of proteins is conferred by their unique structure and their ability to undergo conformational changes upon binding to a substrate or other physiological event. In one study, the structure of proteins was measured using a technique called microcalorimetry. Microcalorimetric studies demonstrated that proteins which are bound to hydrophobic surfaces loose essentially all their cooperatively folded structure compared to the same protein in solution. Because a protein's structure and its ability to undergo conformational changes strongly correlates with biological activity, these data suggest that most proteins that are adsorbed by a hydrophobic surface loose there in vivo biological activity.

Second, the conformation and orientation of immobilized proteins have important effects on the nature of their interaction with cells. D. J. Juliano, S. S. Saaedra and G. A. Truskey, Journal of Biomedical Materials Research 2–7 1103–1113 (1993). Both are influenced by the chemistry and physical properties of the underlying substrate as well as by the method of immobilization. K. Lewandowska, E. Pergament, N. Sukenik and L. A. Culp, The Journal of Biomedical Materials Research 21 1343–1363 (1992).

Third, like in vivo, cells in culture release molecules such as serum proteins and growth factors into the culture media. As discussed above, the secretion and concentration of these molecules in the culture media are critical to the biological function of neighboring cells. Under current cell culture conditions, the careful balance and concentration of secreted molecules are disrupted because secreted molecules are adsorbed by the cell culture surface. Thus, the communication and biological function of cells grown under current cell culture techniques does not mimic in vivo environment.

Finally, the surface concentration of ECM components is a critical factor in the regulation of cell behavior. The ability to control and vary surface biomolecule concentration is therefore of upmost importance and depends on the method of immobilization and in some cases the physical nature of the base material. Simple ECM adsorption to cell culture substrates does not meet these requirements.

In short, to date there is no single method for conjugating proteins to potential cell culture substrates which addresses all these major concerns. Thus, current research is hindered by the fact that cell cultures do not accurately mimic an in vivo environment.

A second problem area created by cell contact is biocompatibility. It is generally acknowledged that artificial biomaterials, including fabricated biomedical polymers, are much less immunologically active than transplants or tissue-derived biomaterials. Nevertheless, the use of non-physiological biomaterials in many lifesaving medical devices, either extracorporeal or implanted, often leads to adverse side-effects for the patient.

The adverse side-effects observed are usually a consequence of contact between cells, proteins, and other biological fluids in the blood with the artificial biomaterial. Typically, contact with the artificial biomaterial activates two major biological processes: coagulation and complement. As discussed above, the complement pathway is designed to destroy the foreign substance and to initiate an inflammatory response in the organism.

Activation of the coagulation cascade can be controlled to a limited extent with the use of anticoagulants, e.g., heparin. Heparin, however, is not well suited for extended use such as in the case of a permanent implant. Further, currently there is no clinically available agent that can prevent or suppress artificial surface-initiated activation of complement. Thus, activation of the coagulation and complement systems upon blood contact is a major problem with respect to biomaterial transplantation.

From the foregoing, it will be appreciated that it would be an advancement in the art to provide a method of coating tissue culture surfaces with ECM proteins or other biomolecules that does not destroy the biological activity of the biomolecule.

It would also be an advancement in the art if the biomolecule coated surface could be used to adhere prokaryotic and eukaryotic cells, viruses, and other molecules for the purpose of biological assay.

It would be a further advancement in the art if the tissue culture cells could adhere and grow on the biomolecule coated surface.

It would be yet another advancement in the art if the biomolecule coated surface did not adsorb proteins and other molecules secreted by the cells in culture.

Finally, it would be an-advancement in the art if biomaterial used in transplantation could be coated with an immunologically inert biomolecule to prevent or minimize host rejection.

Such compositions and methods are disclosed and claimed herein.

4. BRIEF SUMMARY OF THE INVENTION

The present invention is directed at a composition and method for regulating the adhesion of cells and biomolecules to hydrophobic surfaces and hydrophobic coated surfaces. Generally, the composition is an end-group activated polymer (EGAP) generally comprises a block copolymer surfactant backbone and an activation or reactive group. The polymeric block copolymer surfactant of the present invention may be any surfactant having a hydrophobic region capable of adsorbing onto a hydrophobic surface and a hydrophilic region which extends away from the surface when the hydrophobic region is adsorbed to the hydrophobic surface. In one embodiment, the EGAP is synthesized by reacting the block copolymer surfactant with 4-nitrophenylchloroformate followed by 2-(2-pyridyldithio) ethylamine.

A large range of biomolecules can be conjugated to EGAP, include natural or recombinant growth factor, mitogens, growth peptides, differentiating factors, sugars, carbohydrates, polysaccharides, lipids, sterols, fatty acids and nucleic acid. In one embodiment, the biomolecule contains a natural or artificial thiol group. These biomolecules are conjugated to EGAP via a disulfide linkage.

The biomolecule conjugated EGAP surface can be put to a wide variety of uses. For example, the composition can be used to attach organisms and molecules for growth or biological analysis. Briefly, this is done by contacting a hydrophobic surface with an EGAP for a time sufficient for the EGAP to be adsorbed by the hydrophobic surface. A biomolecule is then conjugated to the EGAP adsorbed to the hydrophobic surface to form a biomolecule conjugated EGAP surface. After washing of unconjugated biomolecule, organisms or molecules are placed in contact with the biomolecule conjugated EGAP coated surface such that the organism or molecule adheres to the biomolecule conjugated EGAP coated surface. In one embodiment, the organism or molecule is a eukaryotic or prokaryotic cell, a virus, an antibody or a pharmaceutical drug.

The biomolecule conjugated EGAP surface can also be used to selecting at least one desired organism or molecule from a mixture of at least two organisms or molecules. This is done by first adsorbing EGAP onto a hydrophobic surface. A biomolecule unique for a desired organism or molecule being selected is then conjugated to the EGAP adsorbed to the hydrophobic surface. A mixture of organisms or molecules containing the desired organism or molecule is then contacted with the biomolecule conjugated EGAP coated surface and the desired organism or molecule is allowed to adhere to the unique biomolecule. Finally, non-adhered organisms or molecules are removed.

These and other objects and advantages of the present invention will become apparent upon reference to the accompanying drawings and graphs and upon reading the following detailed description and appended claims.

5. SUMMARY OF THE DRAWINGS

A more particular descriptions of the invention briefly described above will be rendered by reference to the appended drawings and graphs. These drawings and graphs only provide information concerning typical embodiments of the invention and are not therefore to be considered limiting of its scope.

Figure 8A:
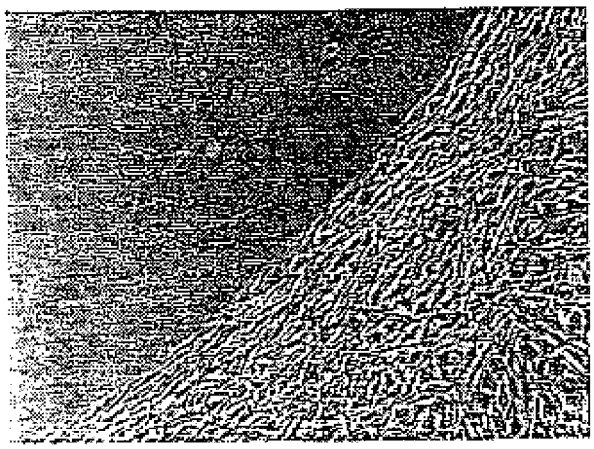
Figure 8B:
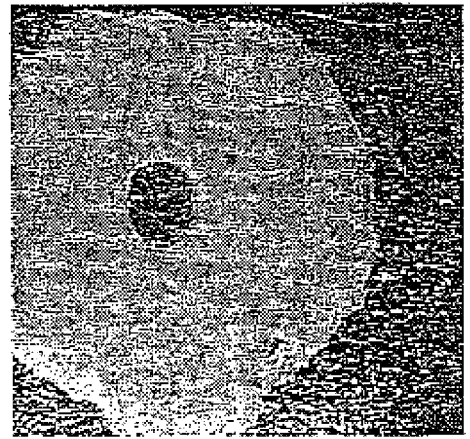

FIG. 8 is a picture illustrating that cells did not attach when seeded on PEO modified surfaces but were found to attach, spread, and proliferate well on unmodified areas. FIG. 8a is a close-up displaying cells aligned at an interface between PEO treated and unmodified areas. In FIG. 8b, cells were fixed and removed from culture well after adequate time to lay down a substantial ECM. A dark spot in the center corresponds to the PEO treated area where there were no cells.

Figure 9:
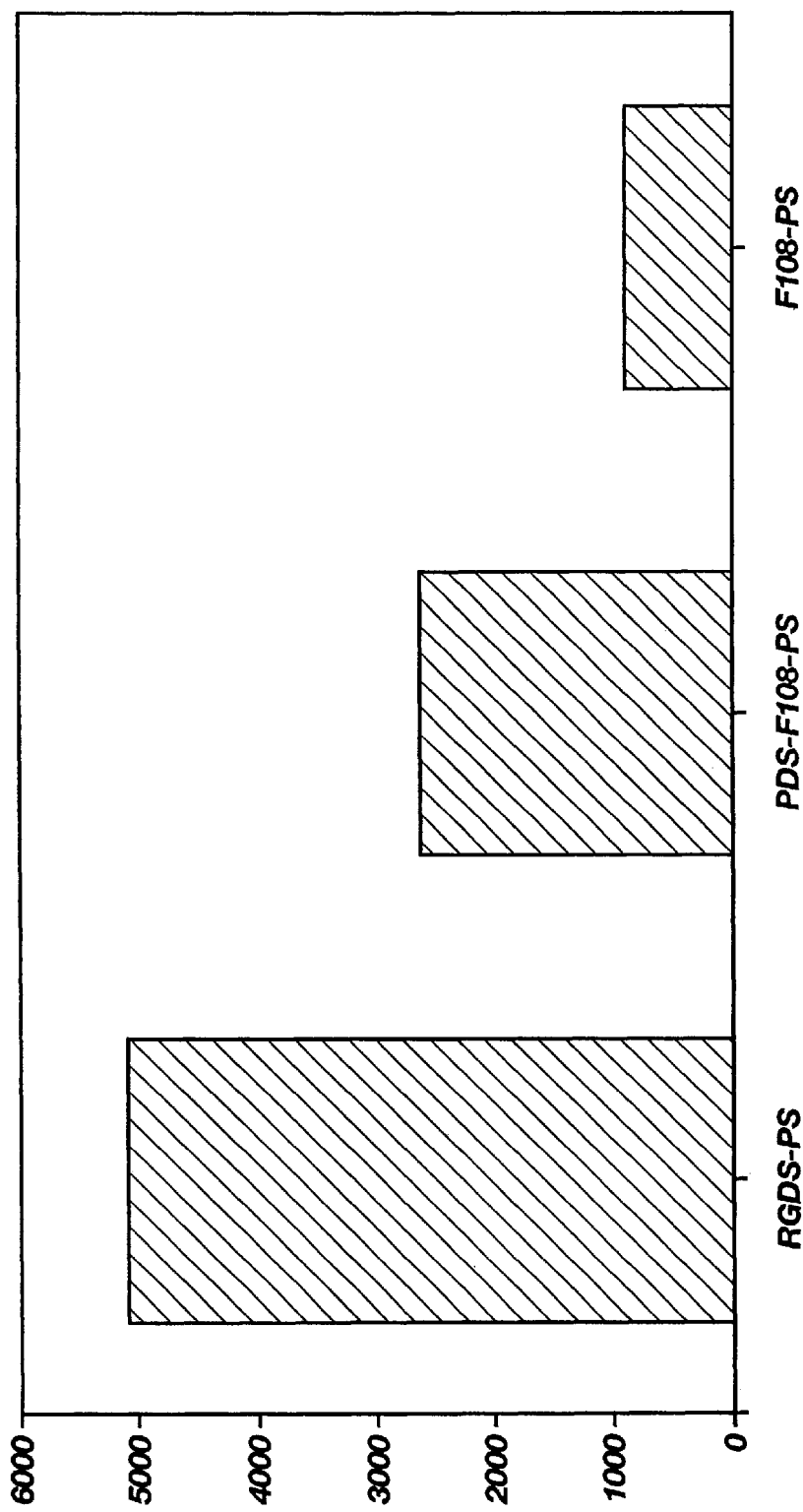

FIG. 9 illustrates that a hydrophobic surface coated with fibronectin peptide RGDS conjugated to EGAP (RGDS-PS) were found to support cell adhesion, (2-pyridyldithio) ethylamine modified EGAP(PDSF108-PS) displayed an intermediate level of adhesiveness, and F108 coated polystyrene was relatively non-adhesive to fibroblast cells.

6. DETAILED DESCRIPTION OF THE INVENTION

The present invention is directed to a novel compound and method for regulating the adhesion of culture cells, organisms, and other biomolecules to a hydrophobic surface. More specifically, the invention is directed to biomolecules that have been conjugated to end-group activated polymer (EGAPs). Biomolecule conjugated EGAPs can be used to coat hydrophobic surfaces making them suitable for a wide range of biochemical and medical uses.

Figure 1:
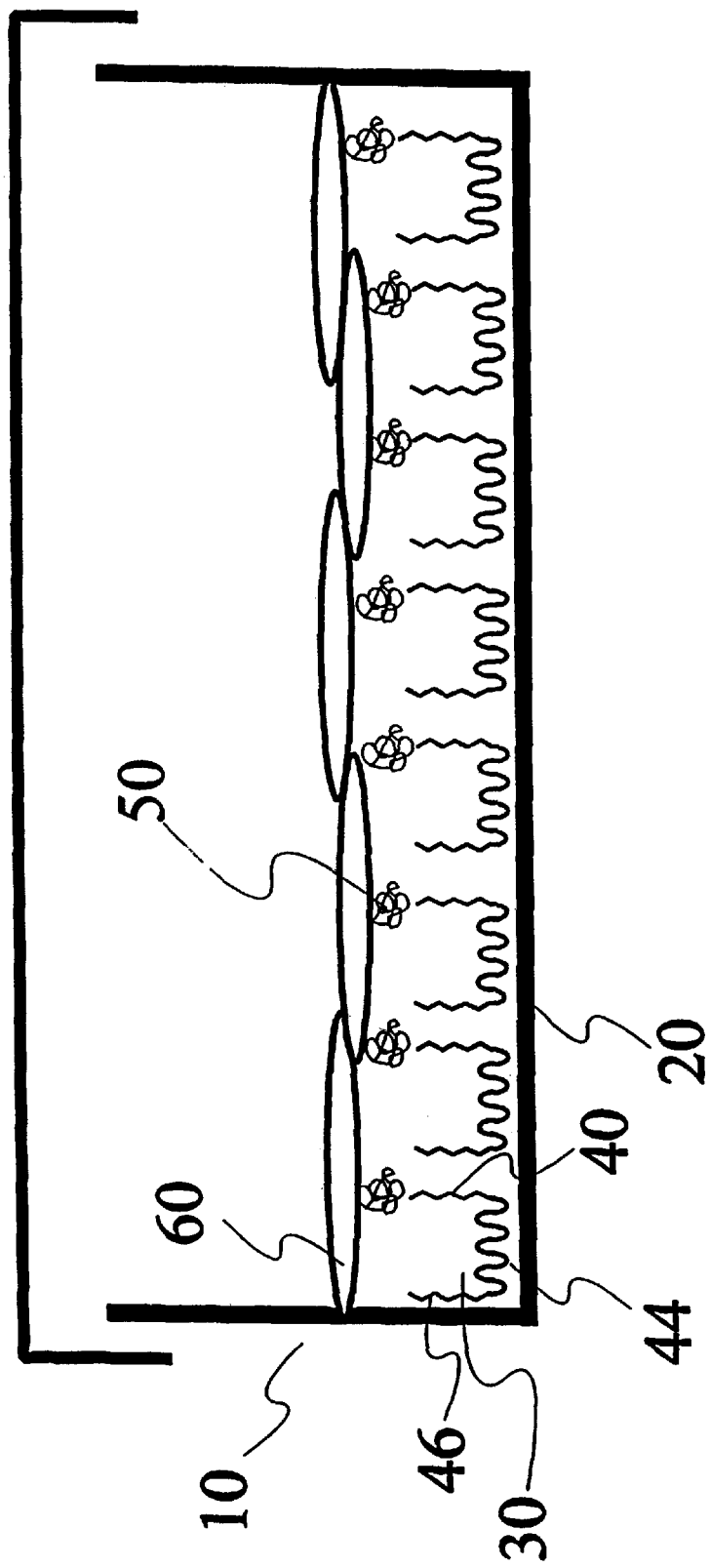
FIG. 1 is a schematic representation of cells attached to a tissue culture surface coated with the composition of the present invention.

Reference is now made to FIG. 1. With reference to FIG. 1, in one preferred embodiment, the present invention is a system 10 for attaching and growing cells in vitro. System 10 generally comprises a hydrophobic tissue culture surface 20, biomolecule conjugated EGAP 30, and cells 60.

System 10 is constructed by first preparing a modified end-group polymer (EGAP) 40. In one embodiment, EGAP 40 comprises a hydrophobic block 44 and two hydrophilic blocks 46. EGAP 40 is modified by, for example, reacting at least one hydrophilic block 46 with 4-nitrophenyl chloroformate followed by 2-(2-pyridyldithio) ethylamine.

EGAP 40 is then applied onto a hydrophobic tissue culture surface 20. Upon application, hydrophobic block 44 of EGAP 40 is adsorbed by hydrophobic tissue culture surface 20. Hydrophilic blocks 46 do not adsorb, however. Instead, hydrophilic blocks 46 extend from the surface in a "sea-weed" fashion. Once EGAP 30 has adsorbed onto the hydrophobic tissue culture surface 20, excess EGAP 30 is removed and tissue culture surface 20 is washed.

Simultaneously, biomolecule 50 is thiolated by methods well known in the art. In one embodiment, biomolecule 50 is thiolated with reduced glutathione. EGAP 40 and biomolecule 50 are then reacted to form biomolecule conjugated EGAP 30. After excess biomolecule conjugated EGAP has been removed and tissue culture surface 20 has been washed, cells 60 are seeded on the biomolecule conjugated EGAP coated surface 20. Cells 60 attach to biomolecule 50, extend processes, and proliferate in an environment that resembles an in vivo setting.

In order to better understand the details of the present invention, the following discussion is divided in six sections: (1) hydrophobic surfaces; (2) EGAP; (3) binding EGAPs to hydrophobic surfaces; (4) suitable biomolecule conjugates; (5) biomolecule conjugated EGAPs; and (6) uses for biomolecule conjugated EGAP coated surfaces.

6.1 Hydrophobic Surfaces

The hydrophobic polymer surfaces of the present invention comprise any suitable polymer or surface coating material which imparts a hydrophobic character to the surface of the substrate. By "hydrophobic" is meant that the surface has a water contact angle greater than about 60', preferably greater than about 70'. Suitable polymers or biomaterials with surfaces having a water contact angle greater than 70' include, but are not limited to polystyrene (PS), polymethylmethacrylate (PMMA), polyolefins (e.g. polyethylene (PE), polypropylene (PP)), polyvinylchloride (PVC), silicones, polyacrylonitrile (PAN), copolymers of polyacrylonitrile/polyvinal chloride, polysulfone, poly (ether sulfone) (PES), certain polyurethanes, pyrolized materials, and block copolymers containing these constituents.

Lesser hydrophobic polymer surfaces (water contact angles between 60' and 70'), such as PVAC are also contemplated by the invention but are less are preferred. Adsorption upon these polymers would be expected to be reduced compared to more hydrophobic polymers such as PS and PMMA. Moreover, detachment of the block copolymer surfactant from the polymer surface over time would be expected. These and non-hydrophobic surfaces, however, may be treated to render them hydrophobic before block copolymer surfactant adsorption. For example, silica can be treated with dimethyl-dichloro silane to provide a hydrophobic surface.

The polymer may be porous or nonporous, or be in the form a flat surface (e.g. a microliter plate), or any suitable shape, such as micro beads, and the like used in chromatography applications. The polymeric surfactant may also be adsorbed upon colloidal or latex particles of a suitable hydrophobic polymer.

6.2 End-Group Activated Polymers (EGAP)

As used herein, the terms end-group activated polymers (EGAP) refers to modified block copolymers surfactants. In one embodiment, the EGAPs of the present invention are of the type defined in U.S. Pat. No. 5,516,703 entitled "Coating of Hydrophobic Surfaces to Render Them Protein Resistant While Permitting Covalent Attachment of Specific Ligands" which is hereby incorporated by reference. Briefly, EGAP is block copolymer surfactant where at least one of the hydrophilic chains has been modified to make it chemically reactive to biomolecules. Accordingly, an EGAP generally comprises a block copolymer surfactant backbone and an activation group or reactive group.

6.2.1 Block Copolymer Surfactant

The polymeric block copolymer surfactant of the present invention may be any surfactant having a hydrophobic region capable of adsorbing onto a hydrophobic surface and a hydrophilic region which extends away from the surface when the hydrophobic region is adsorbed to the hydrophobic surface. In one embodiment, the block copolymer surfactant backbone of EGAP may be in the form of any arrangement of the PEO and PPO blocks with the general formula:

$$(HO-PEO)_a(PPO)_b \qquad (1)$$

where (a) and (b) are integers. Preferably (a) is between 1 and 6, and (b) is between 1 and 3, more preferably (a) is 1 to 2, and (b) is 1. The polymeric block copolymer has a PEO ($-C_2H_4-O-$) content between 10 wt % and 80 wt %, preferably 50 wt % and 80 wt %, and more preferably between 70 wt % and 80 wt %.

The PEO chains or blocks are of the general formula:

$$-(-C_2H_4-O-)_u- \qquad (2)$$

where (u) is the same or different for different PEO blocks in the molecule. Typically, (u) is greater than 50, preferably between 50 and 150, more preferably between 80 and 130. The PPO blocks are of the general formula;

$$-(-C_3H_6-O-)_v- \qquad (3)$$

where (v) may be the same or different for different PPO blocks in the molecule. Typically, (v) is greater than 25, preferably between 25 and 75, and more preferably is between 30 and 60.

The block copolymers may be branched structures and include other structures (e.g. bridging structures, or branching structures) and substituents that do not materially affect the ability of the block copolymer to adsorb upon and cover a hydrophobic surface.

In one embodiment, the block copolymer surfactant used to make EGAP is a polymeric tri-block copolymer with pendant —OH groups, as in Formula (4) below. These tri-block copolymers have a hydrophobic center block of polypropylene oxide and hydrophilic end blocks of polyethylene oxide with terminal —OH groups, and can be represented by the formula:

$$HO-(-C_2H_4-O-)_x-(-C_3H_6-O-)_y-\\(-C_2H_4-O-)_z-H \qquad (4)$$

where (y) is between 25 and 75, preferably between 30 and 60, and (x) and (z) are preferably the same but may be different, and are between 50 and 150, preferably between 80 and 130. Block copolymer surfactants of the type described are commercially available from, for example, BASF.

6.2.2 Activation of the End-Group of a Polymer to Yield an EGAP

The end-group of the polymer is activated by methods well known in the art. Briefly, the —OH end groups of the PEO chains of the polymeric surfactant are modified to introduce a small reactive organic group which is stable in water. Using the block copolymer surfactants represented by equation (4) as an example, if both —OH groups on the pendant PEO chains are substituted, the modified surfactant has the formula;

$$R-O-(-C_2H_4-O-)_x-(-C_3H_6-O-)_y-\\(-C_2H_4-O-)_z-R \qquad (7)$$

where R is a reactive group. Accordingly, the general formula for the modified polymeric surfactants of the invention is:

$$(HO-PEO)_c(R-O-PEO)_d(PPO)_b \qquad (8)$$

where (c+d) is equal to (a) in formula (1), and (c) is 0 or a positive integer, and (b) is defined above for formula (1). The R group may be any reactive group that is stable in water and will impart the desired selective reactivity for the substrate surface when the modified surfactant is adsorbed upon the surface. The specific reactivity may be to any non-water entity or entities.

The R groups are chosen such that they do not significantly impair adsorption of the modified polymeric surfactant on the hydrophobic surface. For example, in a preferred embodiment of the invention, the reactive R group contains a hydrazino group (by further reacting a p-nitrophenyl group), a thiopyridyl group, a tyrosyl residue, or a maleimide. R may also be a member of the group consisting of hydrozino, thiopyridyl, tyrosyl, malcimide, 2-pyridyl disulphide, 5-nitro-2-pyridyl disulphide, 4-pyridyl disulphide, 5-carboxy-2-pyidyl disulphide, and the nitrogen oxides of 2-pyridyl disulfide, 5-nitro-2-pyridyl disulfide, 4-pyridyl disulfide, and 5-carboxy-2-pyidyl disulphide as well as other groups well known in the art.

In another embodiment the R group is for the immobilization of biomolecules and contains the structure:

$$-S-S-R'' \qquad (9)$$

where R" is selected from the group consisting of (1) 2-benzothiazolyl, (2) 5-nitro-2-pyridyl, (3) 2-pyridyl, (4) 4-pyridyl, (5) 5-carboxy-2-pyridyl, and (6) the N-oxides of any of (2) to (5). See U.S. Pat. No. 4,149,003 to Carlson et al. and U.S. Pat. No. 4,711,951 to Axen et al. which are hereby incorporated by reference.

6.3 Binding EGAPs to Hydrophobic Surfaces

Once the EGAP is formed, the EGAP is adsorbed onto an appropriate hydrophobic surface. This simply requires mixing the appropriate amount of EGAP with the hydrophobic surface. Usually approximately two hours is sufficient to completely coat the hydrophobic surface with EGAP. Depending on the shape and size of the hydrophobic surface to be coated, it may be advantageous to shake the mixture to ensure that the entire surface area becomes coated.

Figure 2:
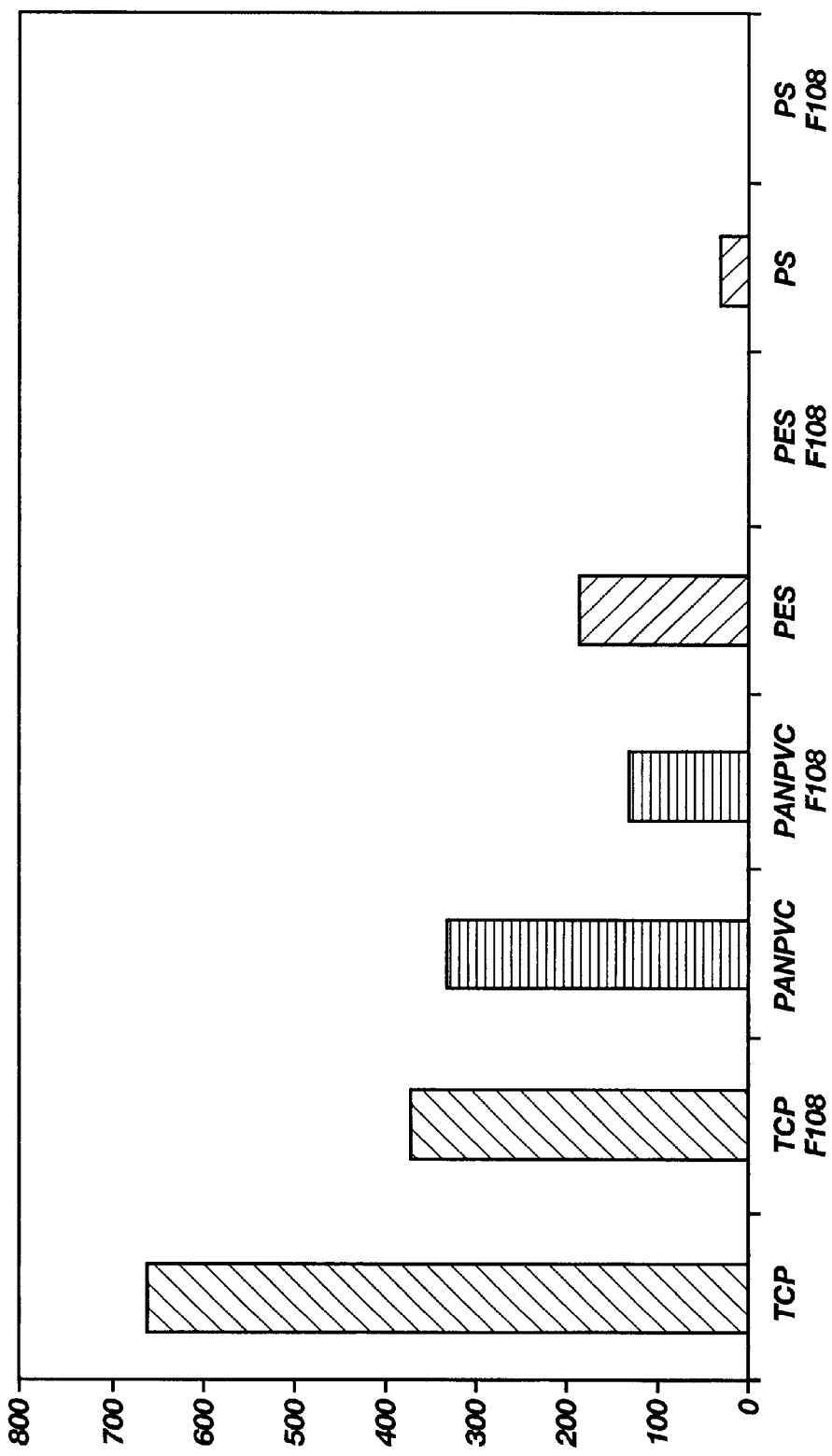
FIG. 2 is a graph illustrating the adhesiveness of NIH 3T3 cells to Pluronic™ F108 coated hydrophobic surfaces.

It will be appreciated that the concentration of EGAP can be regulated by diluting the EGAP with polymer that has not been activated (i.e., block copolymer surfactants). In this way, the number of EGAP reactive sites, and hence, conjugated biomolecules can be regulated. In addition, by using a block copolymer surfactant to dilute the EGAP, the surface does not adsorb cell, proteins and other biomolecules. For example, as illustrated in FIG. 2, various hydrophobic material surfaces coated with a unmodified block copolymer surfactants such as Pluronic™ F108 substantially decrease the adhesiveness of the surface to NIH 3T3 cells.

6.4 Suitable Biomolecule Conjugates

It will be appreciated by one skilled in the art that there is a large number of biomolecules that can be conjugated to EGAP according to the composition and the method of the present invention. As used herein the term biomolecule refers to any molecule that can be conjugated to EGAP, including, but not limited to, proteins, peptides amino acids, nucleic acids, lipids, carbohydrates, and combinations thereof. The biomolecules can be native, recombinant, or synthesized. In fact, the term biomolecule as it is used herein is not limited to naturally occurring molecules, but includes molecules such as synthetic pharmaceutical drugs which have no biological origin.

In a preferred embodiment, the biomolecules are ECM proteins, adhesion proteins, growth factors, or other biomolecules generally used in cell culture. Below is an exemplary review of some of the biomolecules that can be conjugated to EGAP and used according to the present invention.

6.4.1 Extracellular Matrix Proteins

EGAP could be conjugated to an ECM protein. For example, EGAP could be conjugated to one or more of the various collagen molecules currently known or hereafter isolated. Collagen is the name given to a superfamily of ECM proteins whose primary role is forming and preserving the structural integrity of the ECM and cells. Collagen's characteristic triple-helix domain forms fibrils, filaments, or networks, either alone or in combination with other ECM components.

Collagen IV is a major component of basement membranes and forms a network to which other basement components, such as laminin, nidogen, heparin and heparan sulfate proteoglycans, interact. Many cells types adhere to Type IV collagen. See, e.g., Glansville, R. W. "Structure and Function of Collagen Types," Academic Press Inc., pp. 43–79. Moreover, regions within Type IV collagen are known to promote or inhibit cell adhesion. Vandenberg et al., *J. Cell Biol.*, 113: 1475–1483 (1991); Tsilibary et al., *J. Cell Biol.* 111: 1583–1591. Surfaces coated with Type IV collagen (or specific regions or Type IV collagen) conjugated EGAPs, therefore, could be used to both promote and inhibit cell attachment and growth in vitro.

Type IV collagen can be obtained from basement membranes treated with pepsin or with bacterial collagenase. Glansville, R. W. "Structure and Function of Collagen Types," Academic Press Inc., pp. 43–79; Hudson, et al., "Extracellular Matrix Macromolecules—A Practical Approach" (M. A. Haralson and J. R. Hassell, eds.) IRL Press, in press. Moreover, the complete primary structures of mouse and human a(IV) and a2(IV) chains have been deduced from cDNA sequences and mouse and human a(IV) and a2(IV) genomic clones have been extensively characterized. Vuorio et al., Annu. Rev. Biochem. 59: 837–872 (1990); Sandell, L. J. and Boyd, C. D., "Extracellular Matrix Genes" (L. J. Sandell and C. D. Boyd, eds.) Academic Press Inc. pp. 1–56 (1990); Blumberg, B. and Kurkinen, M. "Extracellular Matrix Genes (L. J. Sandell and C. D. Boyd, eds.) Academic Press Inc., pp. 115–135 (1990). The corresponding polypeptides coded by these genes, therefore, could be obtained using recombinant techniques well known in the art.

In another example, the biomolecule could be a fibrillar collagen which includes five different molecular types (I, II, III, V, and XI). Fibrillar collagens polymerize to form fibrils that serve as stabilizing scaffolds in extracellular matrices. Cell attachment, differentiation, and migration are influenced by fibrillar collagens. It has been shown that fibrillar collagens interact with cells through receptors on the cell surface. See e.g., Hemler, M. E., *Annu. Rev. Immunol.* 8: 365–400 (1990).

Surfaces coated with fibrillar collagen conjugated EGAPs, therefore, would promote cell attachment, differentiation and migration and better mimic in vivo biological conditions. Fibrillar collagen is commercially available from, for example, Sigma, St. Louis, Mo. Moreover, methods of purifying, as well as cDNAs coding fibrillar collagen, are well known in the art. (See e.g., Vuorio, et al. *Annu. Rev. Blochem.* 59: 837–872 (1990).)

EGAP could also be conjugated to one or more fibronectin molecules or peptides thereof. The subunits of fibronectins vary in size between approximately 235 and 270 kDa plus carbohydrates. Extended polypeptide segments in certain parts of the molecule are highly susceptible to proteolysis, which generates a series of protease resistant domains, each comprising several of the repeating modules. These domains contain a variety of binding sites for other molecules, including collagens, fibrin, heparin/heparan sulphate, and cell surface receptor integrins.

Fibronectins are widely expressed in embryos and mature cells, especially in regions of active morphogenesis, cell migration, and inflammation. Fibronectins promote the adhesion and spreading of many cell types by binding to several different integrin receptors. See, e.g., Hynes, R. O., *Cell* 48:549–554 (1987). Tumor cells show reduced levels of fibronectin and levels in plasma fall in various forms of trauma. In contrast, fibronectin levels are elevated during wound healing and fibrosis.

Fibronectin conjugated EGAPs, therefore, could be used in tissue culture to assist in cell adhesion, morphogenesis, and cell migration. Moreover, biomaterials, such as surgical wraps, could be coated with fibronectin conjugated particles to aid and accelerate wound healing.

The full length polypeptide of fibronectin, like many other proteins, is not required for many of the activities and properties described above. For example, it is known that fibronectin has two cell binding sites which are recognized by two different integrin receptors. The first cell binding site comprises three residues: arginine-glycine-aspartic acid, or RGD. The second cell binding site comprises the peptide: glutamic acid-isoleucine-leucine-aspartic asid-valine, or EILDV. Many of these peptide, including RGD, RGDS, RGES, RFDS, GRDGS, and GRGS are commercially available from, for example, Sigma, St. Louis, Mo.

Other peptides such as GRGDTP inhibit cell attachment of fibronectin, vitronectin, and Type I collagen. Amino acid sequence QPPRARI is the binding site for the carboxy-terminal heparin binding domain. Peptides that inhibit platelet aggregation and inhibit fibronectin binding to bacteria are also well known and commercially available. EGAP, therefore, can be simply conjugated with any number of peptides or domains to obtain the desired results according to the present invention.

In another example, EGAP could be conjugated to agrin. Agrin is ECM glycoprotein which can take the form of either a 150 kDa or a 95 kDa protein. Agrin is localized at the neuromuscular junction and induces clustering of acetylcholine receptors on skeletal myotubes in cell culture. Clustering of this receptor is one of the most dramatic events in neuromuscular synapse formation and regeneration in vivo. Purified agrin has been shown to induce clustering of synaptic molecules in vitro, such as ECM-associated acetylcholinesterase and membrane-associated acetylcholine receptors, and it is very likely to function similarly in vivo.

As an agent that induces differentiation in skeletal myotubes, agrin is synthesized in motor neurons and transported to their terminals in skeletal muscles. Agrin has been shown to induce phosphorylation on tyrosine on the acetylcholine receptor β-subunit. Treatments that inhibit receptor aggregation prevent tyrosine phosphorylation. Results suggest that the agrin receptor regulates a tyrosine protein kinase or phosphatase that in turn regulates receptor clustering. These and other data demonstrate that the extracellular matrix protein agrin contains all the essential information needed to form a neuromuscular synapse. Therefore, the ability to conjugate agrin to EGAP to form an agrin conjugated EGA would be a significant advancement in co-culture cell technology. This, together with the fact that conjugated block copolymer surfactant surfaces do not adsorb secreted cellular products that could be important for differentiation and growth, would approximate an in vitro system to study the formation and function of the neuromuscular junction. Understanding the formation of the neuromuscular junction is the first step in understanding the formation of more complex synapses in the central nervous system.

Agrin can be obtained from the basal-lamina enriched fraction of *T. Californica* electric organ as described in Nitkin et al., *J. Cell Biol.,* 105: 2471–2478 (1987). Alternatively, portions of agrin glycoprotein can be obtained from available cDNAs using recombinant techniques well known in the art. Tsim et al., *Neuron,* 8: 677–689 (1992). Monoclonal antibodies against *T. Californica* agrin are also available. Reist et al. *J. Cell. Biol.,* 105: 2457–2469 (1987).

In addition, one skilled in the art will appreciate that other ECM components and proteins, such as aggrecan, biglycan, bone sialoprotein, cartilage matrix protein, Cat-301 proteoglycan, CD44, cholinesterases, FACIT collagens (Type IX, XII, XIV), other collagens (Type VI, VII, XIII), short chain collagens (Type VIII, X), decorin, elastin, fibrinogen, fibroglycan, fibromodulin, fibulin, glypican, HB-GAM, hyaluronan and hyaluronan binding proteins, J1 glycoproteins, laminin, laminin binding proteins, link protein, mucins, nidogen/entactin, osteopontin, perlecan, plasminogen, plasminogen activator inhibitor 1, plasminogen activator inhibitor 2, proteins containing $Ca^{2+}$-dependent carbohydrate recognition domains, restrictin, serglycin, SPARC/osteonectin, syndecan, tenascin, thrombospodin, tissue-type plasmogen activator, urokinase type plasminogen activator, versican, vitronectin, and von Willebrand Factor could be conjugated to EGAP and used in numerous biological processes and assays.

6.4.2 Cell Adhesion Molecules

Cell adhesion molecules are molecules that, in addition to mediating cell-ECM contact, mediate cell—cell contact. Cell adhesion is required at all stages in development and critical to the overall organization of tissues and organs. To date, there have been hundreds of cell adhesion molecules isolated and characterized. These molecules can be roughly categorized into five protein superfamilies: (1) the immunoglobulin (Ig) superfamily; (2) the cadherin superfamily; (3) the integrin superfamily; (4) the selectin superfamily; and (5) the H-CAM superfamily.

The Ig superfamily, for example, which includes other proteins such as CAM and N-CAM are primarily involved in cellular recognition. As such, immunoglobulins or antibodies play a critical role in proper immune function. See Williams et al., *Ann. Rev. Immunol.* 6: 381–405 (1988). As will be discussed below, the Ig superfamily of molecules forms the bases for immunoassays in the art.

The feasibility and value of conjugating adhesion protein of the immunoglobulin superfamily to EGAP has been demonstrated. U.S. Pat. No. 5,516,703. In one embodiment, a significant increase in antigen binding was observed when anti-IgE was immobilized to a polystyrene surface via an EGAP tether rather than immobilization through simple adsorption as is the common practice in the art today. In fact, antigen binding to anti-IgE conjugated EGAP was on average 4 times greater that anti-IgE adsorbed to the PS surface.

The same strategy could be used to conjugate numerous adhesion proteins to EGAP for the purposes of biological analysis or cell growth. Examples include AMOG, cadherins, CD2, CD4, CD8, C-CAM (CELL-CAM 105), cell surface galactosyltransferase, connexins, desmocollins, desmoglein, fasciclin I, fasciclin II, fasciclin III, F11, GP Ib-IX complex, integrins, intercellular adhesion molecules, L1, leukocyte common antigen protein tyrosine phosphate (LCA, CD45), LFA-1, LFA-3, mannose binding proteins (MBP), MUC18, myelin associated glycoprotein (MAG), neural cell adhesion molecule (NCAM), neurofascein, neruoglian, neurotactin, PECAM-1, PH-20, selectins, TAG-1, VCAM-1 and the like. In fact, hundreds of immunoglobulin proteins directed at different cellular components are commercially available from, for example, Sigma Chemical COW'S., St. Louis, Mo.

6.4.3 Growth Factors, Mitogens, and Differentiation Factors

Cell contact with a number of different biomolecules, such as growth factors, mitogens, and differentiation factors can stimulate cell division. Many of these biomolecules are normally present in growth serum used in most cell culture media. Others biomolecules, like some bacterial lipopolysaccharides and certain cell agglutinating proteins (lectins), are not present in normal growth media. Nevertheless, they are an integral part of work aimed at discerning what signals regulate cell growth and thus have huge implications in cancer research.

For example, platelet-derived growth factor (PDGF), would be an ideal candidate to conjugate to EGAP. PDGF is the major polypeptide mitogen in cell culture serum. In fact, studies in fibroblast demonstrate that PDGF is required to make cells competent to other growth factors. That is, the cell will not respond to other growth factors and mitogens unless they are first exposed to PDGF.

In vivo, PDGF is stored in the α granules of the blood platelets. During blood clotting and platelet adhesion, PDGF is released from these α granules. The release of PDGF at the site of injury causes some cell types to migrate to the site of injury and causes other cell types to divide. Accordingly, PDGF conjugated EGAPs could be used to promote cell growth in culture. In addition, PDGF could be used to promote wound healing in vivo by applying it to wounds in conjunction with an appropriate biomaterial. The PDGF would be tethered to EGAP which in turn would be adsorbed to the biomaterial. Thus, unlike other drug delivery methods, the amount of PDGF stimulation and the site of stimulation could be tightly regulated.

In addition, one skilled in the art will appreciate that other growth factors and mitogens, such as EGF, TGF-α, TGF-β, NGF, IGF-I, IGF-II, GH, and GHRF can also be conjugated to EGAP according to the method of the present invention and be used for cell culture and a variety of biological assays.

Another group of biomolecules that could be conjugated to EGAP are differentiating factors. These factors determine the fate of precursor cells, such as stem cells. For example, depending on the differentiating factor or factors which a stem cell is exposed, a stem cell can become a plasma cell, a memory B lymphocyte, an activated T cell, a macrophage, blood platelets, or a erythrocyte.

These factors, therefore, have tremendous implications in vitro and in vivo. In vitro, stem cells could be grown on one or more of these factors conjugated to EGAP. As such, the fate of the cell can be carefully controlled. For example, the ability to regulate T cell production in vitro from precursor cells could be used to supplement the loss of T cells that leads to acquired immunodeficiency syndrome (AIDS). In vivo, the differentiating factor erythropoietin is currently being used to increase red blood cell production in patients that have lost large volumes of blood.

In addition, one skilled in the art will appreciate that other differentiating factors and proteins, such as multi-CSF (Il-3), GM-CSF, G-CSF, and M-CSF can also be conjugated to EGAP.

6.4.4 Nucleic Acid

Nucleic acids can also be conjugated to EGAPs. Nucleic acids as the term is used herein refers to molecules comprised of natural and synthetic DNA and RNA molecules. One skilled in the art will appreciate that DNA and RNA can be modified or conjugated without disturbing its biological activity. Moreover, nucleic acids of various lengths can be easily synthesized and linked together using synthesis and ligation techniques commercially available and well known in the art.

A common strategy in the art is to substitute one of the nucleotides or bases in a DNA with a universal base. A recent publication, for example, describes the properties of 3-nitropyrrole 2'-deoxynucleoside when used as universal nucleoside. Briefly, 3-nitropyrrole 2'-deoxynucleoside can be used for many purposes, including sequencing, PCR, ligase chain reaction, in situ hybridization, mutagenesis, motif cloning, and even in RFLP. 3-Nitropyrrole 2'-deoxynucleoside is commercially available form, for example, Bio-Synthesis, Lewisville, Tex.

In a preferred embodiment, the nucleic acid is modified with a free thiol group. The free thiol group has been shown to be reactive towards maleiimide or an iodoacetyl-derived conjugate. Binding of alkaline phosphatase, horseradish peroxidase, and various fluorophores to synthetic oligonucleotides by means of a free thiol group has been reported in the literature. Nucleic acids with 5' thiol C6, 3' thiol C3 S—S, and 5'/3' thiol C6 S—S base modifications are commercially available form, for example, Bio-Synthesis, Lewisville, Tex.

Also, commercially available are technologies for attaching reactive amine groups at the 5' terminus, 3' terminus, or any internal position. The Amino-I, and Amino-II can incorporate a primary aliphatic amine functional groups into oligonucleotides at single or multiple sites. Many of these analog are suitable for attaching the DNA to other molecules, e.g., EDTA or alkylating reagents which can cut the complementary strand or double strand. Other examples include 5'-C3 amine, 5'-C12 amine, 3'-C3 amine, 3'-C7 amine, amino C6 dT, amino I, amino II, 3'-DMT-C6 amine, amino C2 dT which are commercially available from, for example, Bio-Synthesis, Lewisville, Tex.

Vaious other base modifications include deoxy inosine (dI), deoxy uridine (dU), 5-methyl-dC, O-6-ME-dG, 5-I-dU, 5-I-dC, 5-Br-dU, 3-nitropyrrole (M), 3'-dA (cordycepin), 2', 3'-ddC, TMP-F-dU, 04-triazolyl-dT, 06-phenyl-dI, 2-aminopurine, 04-triazolyl-dU, 7-deaza dG, N-6-Me-2'dA, S6-DNP-dG, 5'-OMe-dT, ethano-dA, 5' or 3' phosphorylation, 3'-spacer C3, carboxy-dT are commercially available from, for example, Midland, Midland, Tex. and Bio-Synthesis, Lewisville, Tex.

6.5 Biomolecule Conjugated EGAP

Biomolecules can be conjugated to EGAP using numerous methods known in the art. By reacting hydroxylated block copolymer surfactants with 4-nitrophenyl chloroformate, one can efficiently conjugate biomolecules having a variety of reactive groups. For example, EGAPs react relatively easily in an organic solvent with amino groups, 2-pyridyl disulfides, peptide, hydrazino and other amino containing molecules. Using hydrazino groups as the bridge, tyrosyl groups for radioisotope labeling purpose can be subsequently coupled to the EGAP by a reaction with the Bolton-Hunter reagent.

Biomolecules are conjugated via amine groups. In one embodiment, 4-nitrophenyl chloroformate activated EGAP was conjugated to a biomolecule via an amine group on a peptide. The peptide glycyltryptophan (Gly-Trp) was mixed with an appropriate amount of 4-nitrophenyl chloroformate activated EGAP. The two compounds were allowed to react at 25° C. overnight. The reaction mixture was then purified by passing it through a Sephadex column. Gly-Trp conjugated EGAP was confirmed by dry weight and photometric analysis.

Biomolecules can also be conjugated to EGAP via a disulfide bond. EGAP molecules, as discussed above, can be activated by introducing a reactive group containing a disulfide derivative such as a 2-(2-pyridyldithio)ethylamine. This method of conjugation is preferred because the rate of hydrolysis of the 2-pyridyl disulfides groups at about pH 8.5 is almost negligible in comparison to the rate of the thiol-disulfide exchange reaction. As such, only a small concentration of biomolecule is required.

Moreover, this conjugation method provides an easy way to detect the degree of biomolecule conjugation. The reaction between the thiol group on the biomolecule and 2-(2-pyridyldithio)ethylamine releases thiopyridone. Thiopyridone concentration can be readily and accurately quantified by spectroscopic detection at 343 nm with an extinction coefficient of $8060/cm^{-1}M^{-1}$. Thus, the concentration of thiopyridone is directly proportional to the degree of biomolecule conjugation.

Finally, since the thiol-disulfide exchange is a reversible reaction, bound biomolecules can be released from the solid phase by addition of a thiol-containing reagents, such as dithiothreitol (DTT).

Figure 4:
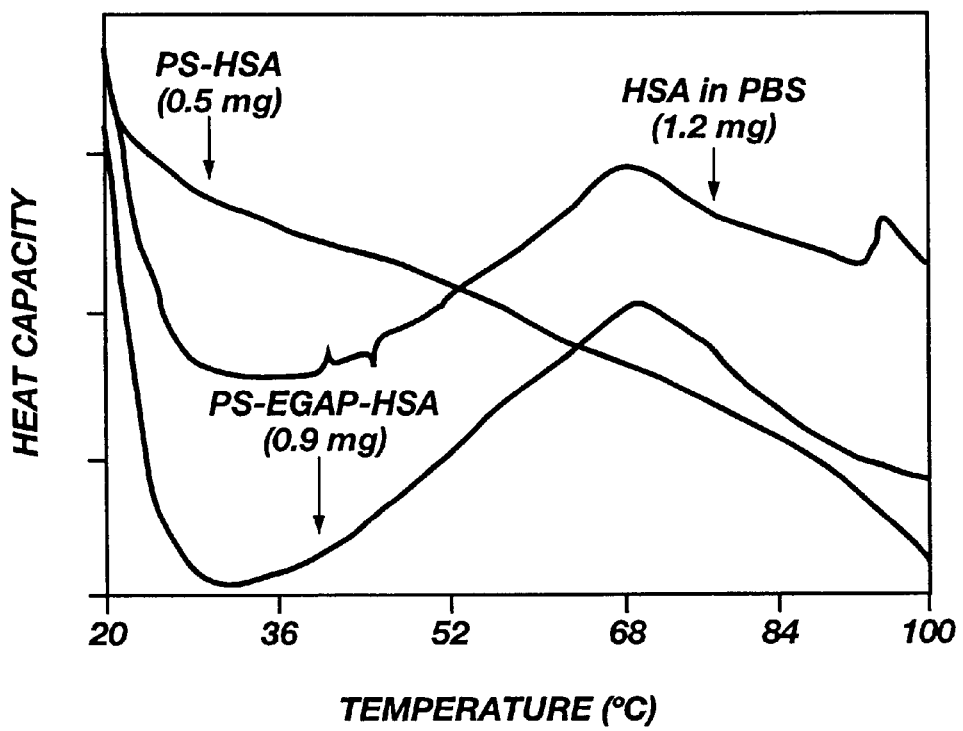
FIG. 4 is a graph illustrating the thermal stability of human serum albumin (HSA) free in phosphate buffered saline solution (HSA in PBS), adsorbed by a hydrophobic surface (PS-HSA), and conjugated to EGAP coated hydrophobic surface (PS-EGAP-HSA).
Figure 5:
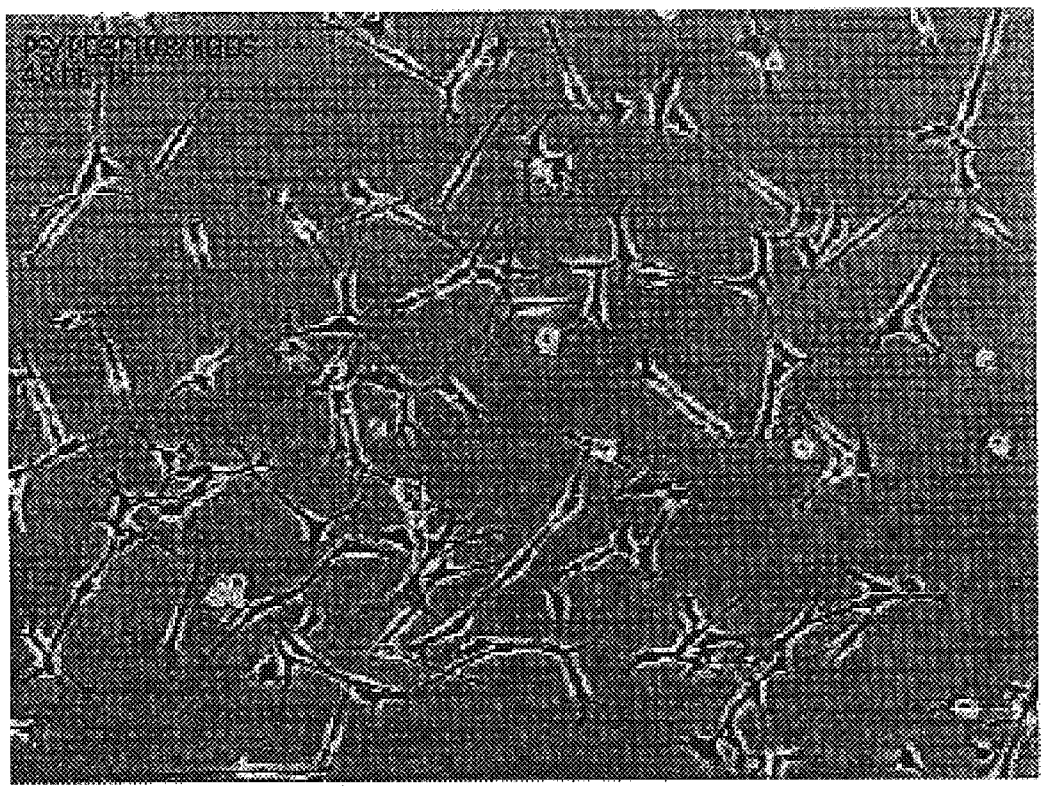
FIG. 5 is a picture of fibroblast cells attached and growing on a fibronectin peptide GRGDSY conjugated EGAP coated surface.

In one embodiment, the biomolecule fibronectin and human serum albumin was conjugated to EGAP using the methods described above. As illustrated in FIGS. 4 and 5, microcalorimetry studies indicate that these biomolecules retain their native secondary structure when tethered to EGAPs.

6.6 Uses for Biomolecule Conjugated EGAP Coated Surfaces

It will be appreciated by one skilled in the art that given the large number of biomolecules that can be conjugated to EGAP, the number of uses for biomolecule conjugated EGAPs is also large. Below are exemplary uses for biomolecule conjugated EGAPs.

6.6.1 Method of Attaching and Growing Cells

The composition and the method of the present invention can be used to attach and grow cells in culture. As discussed above, EGAP can be conjugated to any number of ECM and cell adhesion proteins as well as growth and differentiation factors.

Figure 6:
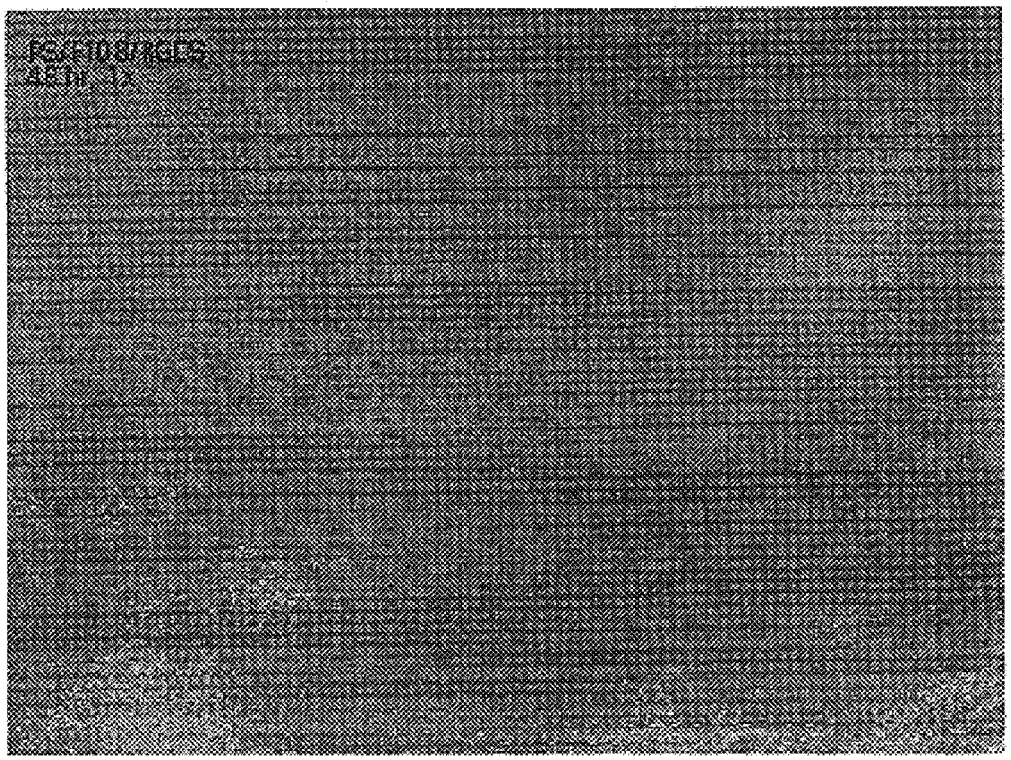
FIG. 6 is a picture illustrating that fibroblast cells were unable to attach to unconjugated EGAP coated surface.

In one embodiment, NIH 3T3 cells were grown on hydrophobic culture surface coated with GRGDSY conjugated EGAP. GRGDSY is a peptide corresponding to a cell binding site of fibronectin. The GRGDSY was conjugated to an F108 derivative EGAP via a disulfide bond prepared according to the 2-pyridyl disulfide conjugation method described above. Once the GRGDSY was conjugated to EGAP and the hydrophobic surface was washed, NIH 3T3 cells were seeded at a concentration of $6 \times 10^3$ cells/cm$^2$ in DMEM supplemented with 10% bovine serum. Qualitatively, as illustrate in FIG. 5, fibroblast cells were in good health and were able to attach extend processes in GRGDSY conjugated EGAP. On the contrary, as illustrated in FIG. 6, no attachment was observed on cells seeded on unconjugated F-108.

Figure 7:
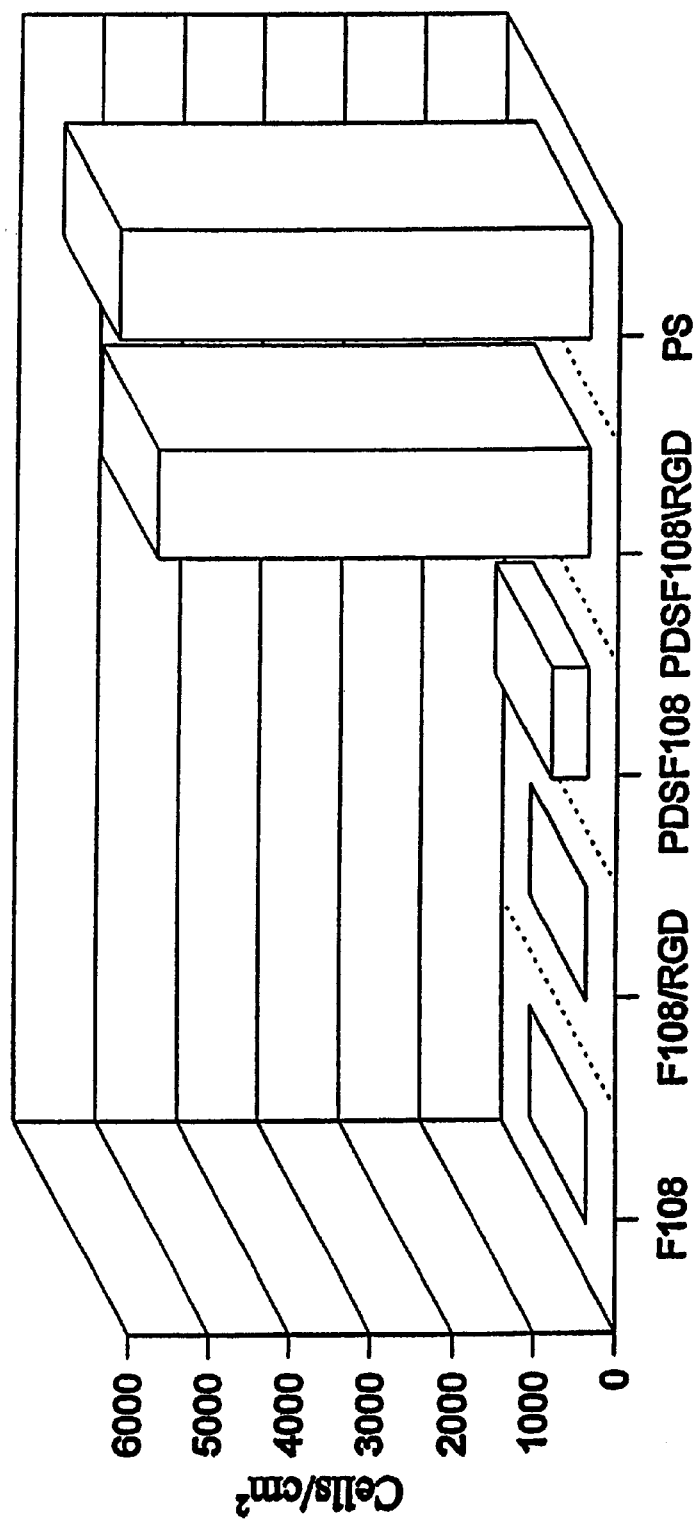
FIG. 7 is a graph illustrating the adhesion of cells to surfaces coated with F-108 (F108), F-108 containing unconjugated GRGDSY (F108/RGD), 2-pyridyl disulfide conjugated F-108 (PDSF108), GRGDSY conjugated EGAP (PDSF108/RGD), and untreated polystyrene (PS).

Quantitatively, as illustrate in FIG. 7, nearly the same number of cells attached to GRGDSY conjugated EGAP (PDSF108/RGD) as attached to untreated polystyrene (PS). Moreover, cell attachment and growth is directly related to the GRGDSY conjugated EGAP as very little attachment, if any, was found when the surface was coated with F-108 (F108), F-108 containing unconjugated GRGDSY (F108/RGD), and 2-pyridyl disulfide conjugated F-108 (PDSF108).

It will be appreciated by one skilled in the art that the same principles and methodologies could be used to grow other cells, including other eukaryotic cells such as insect cells, yeast and plant cells, and prokaryotic cells such as bacteria.

6.6.2 Method for Selecting and Sorting Cell and Other Biological Material

The composition and the method of the present invention can be used to sort cells and other biological material. It will be appreciated by one skilled in the art that it is often desirable to select one cell type from a mixture of cells. For example, identifying lymphocytes as either T cells or B cells is useful in diagnosing various diseases, including lymphoproliferative malignancies, immunodeficiency diseases, unexpected infections diseases, monitoring of transplants, and acquired immunologic disorders such as AIDS. Current methods involve a combination of density gradient centrifugation and either fluorencence microscopy or cell flow cytometry (or fluorescence-activated cell sorter). These methods are tedious and expensive. Moreover, the stress of the procedure often damages the cells making it difficult, if not impossible, to grow the cells once they have been selected.

The method of the present invention could be used to quickly sort cells. EGAP could be conjugated to a number of biomolecules that are specific for the desired cells type. For example, the biomolecule could be a monoclonal antibody against a specific cell surface antigen such as a transmembrane receptor or a particular carbohydrate moiety. Many of these biomolecules, including CD2, CD3, CD4, CD8 on T cells and CD 19, CD20, CD2, and surface immunoglobulins on B cells are all commercially available from, for example, Sigma Chemical Company, St. Louis, Mo.

In one embodiment, the cell specific biomolecule conjugated EGAP is coated on polystyrene beads. The polystyrene beads are then combined with a mixture of cells under appropriate incubation conditions and growth media that does not contain molecules that will bind to the cell specific biomolecule. After the cells have had an opportunity to bind to the cell specific biomolecule, the polystyrene beads are separated from the remaining unattached cells. The separation means is any means well known in the art including magnetic, streptavidin separation, or mechanical separation such as gentle centrifugation. In one embodiment, a subpopulation of the EGAPs coated to the polystyrene beads comprises biotin conjugated EGAP. Therefore, the biotin is available for binding and separation with streptavidin, such as streptavidin MagneSpheres® paramagnetic particles sold by Promega, Madison, Wis. After several gentle washes to remove non-specifically bond cells, the collected polystyrene beads are assayed directly using common bioassays well known in the art or cultured. These methods of cell sorting are only exemplary of the many cell sorting methods that can be used with the composition and method of the present invention.

6.6.3 Biological Assays

6.6.3.1 Immunoassays

As discussed above, after infection with a pathogen, the immune system recognizes the pathogen as foreign and begins to produce large quantities of antibodies against the pathogen. The antibodies bind to the pathogen and initiate other immune functions which are aimed at eliminating the pathogen from the organism.

Thus, a common way of determining whether a given individual is infected with a certain pathogen, such as HIV, is to assay for the presence of antibodies against HIV in the individual's blood. There are many types of immunoassays known in the art. The most common types of immunoassays are competitive and incompetitive heterogeneous assays such as enzyme-linked immunosorbent assays (ELISA). In immunoassays the reactant is an antigen. In a noncompetitive ELISA, unlabeled antigen is commonly bound to a hydrophobic surface through adsorption. Biological sample is combined with antigens bound to the surface and antibodies (primary antibodies) in the biological sample are allowed to bind to the antigens forming immune complexes. After immune complexes have formed, excess biological sample is removed and the reaction cells are washed to remove nonspecifically bound antibodies. Immune complexes are then reacted with an appropriate enzyme-labeled anti-immunoglobulin (secondary antibody). Anti-immunoglobulins recognize bound antibodies, but not antigens. Anti-immunoglobulins specific for antibodies of different species, including human, are well known in the art and commercially available from Sigma Chemical Company, St. Louis, Mo. and Santa Cruz Biotechnology, Santa Cruz, Calif. After a second wash step, the enzyme substrate is added. The enzyme linked to the secondary antibody catalyses a reaction which converts substrate into product. When excess antigen is present, the amount of catalyzed product is directly proportional to the amount of antigen specific antibodies (analyte) in the biological sample. Typically, the reaction product is colored and thus measured spectrophotometrically using UV/VIS technology and equipment well known in the art.

Biomolecule conjugated EGAP's are suitable for immunoassay technology as illustrated by data using IgE.

6.6.3.2 Method of Immobilizing Virus for Analysis

The present invention may also be used to collect viruses for various uses, including growth and bioassay. For example, as discussed above, a common way of detecting whether an individual has been infected with a particular pathogen was to assay for antibodies against the pathogen in the individual's blood. Many times, however, this technique is unsuitable. For example, diagnosing of HIV infection in infants is difficult due to the placental passage of IgG antibodies from the infected mother to the child. Moreover, there is a window between the time an individual becomes infected with a pathogen and the development of a detectable antibody producing immune response. Using immunoassays, an individual who is in fact HIV positive may test negative for HIV because the level of HIV specific antibodies are not detectable when the test is administered. Therefore, infants and some other individuals are tested for HIV infection using PCR techniques, a sensitive technique which assay for HIV DNA rather than antibodies against HIV.

In order to assay for HIV DNA, a quantity of virus must be obtained. Currently this is done by taking a small portion of the individual's blood. However, the amount of non-viral DNA in the individual's blood decreases the sensitivity, specificity, and background of the assay. It would be an advantage, therefore, to enrich the sample for virus before a DNA-based assay such as PCR is performed.

The present invention provides such means. EGAP adsorbed to a hydrophobic surface is conjugated to a biomolecule which is specific for HIV such as antibodies against gp 120, a glycoprotein which is expressed on the surface of the virus. The individual's blood is, for example, passed through a column containing polystyrene beads adsorbed with gp120 conjugated EGAP. HIV viruses bind to gp 120 conjugated EGAP while other blood components pass through the column. After a series of low salt washes, the polystyrene beads containing bound HIV are assayed using PCR technology well known in the art.

Generally, oligonucleotide primers to conserved regions of HIV genes, such as the gag and pol genes, are synthesized and used to amplify a region of the viral gene. The amplified PCR product is then denatured and a radiolabelled DNA probe is added and permitted to hybridize with the amplified product. The hybridized product is identified by running the mixture on a polyacrylamide gel followed by autoradiography.

Recently, PCR techniques employing tris-bipyridineare ruthenium (II) complexes have greatly facilitated the procedure and sensitivity of PCR techniques and thus are also contemplated by the present invention. See Kenten, J. H., et al. "Rapid Electrochemiluminescence Assays of Polymerase Chain Reaction Products", *Clin. Chem.*, 37: 1626–1632 (1991); T. E. Schutzbank & J. Smith, "Detection of Human Immunodeficiency Virus Type 1 Proviral DNA by PCR Using an Electrochemiluminescence-tagged Probe," *J Clin Microbiol* 33: 2036–2041 (1995) which are hereby incorporated by reference. Briefly, oligonucleotide primers directed at conserved regions of an HIV gene are synthesized and used to amplify a region of that gene. One of the oligonucleotides is biotinylated (linked to a biotin molecule) by methods well known in the art. The amplified PCR product is then denatured and hybridized with an ECL-labeled DNA probe which is complementary to the amplified biotinylated DNA stand. After an appropriate hybridization period, the biotinylated-DNA/ECL-labeled DNA hybrid is reacted with streptavidin coated magnetic particles. A magnetic force is applied to retain the biotinylated-DNA/ECL-labeled DNA hybrids in the reaction vessel while unhybridized material is removed. Finally, the ECL complexes are excited by chemical, photometric, or electrical means and the photon emission measured.

The above example is merely exemplary for how the present invention can be used to enrich biological samples for viruses for use in biological assays and for growth using techniques well known in the art.

7. EXAMPLES

The following examples are given to illustrate various embodiments which have been made with the present invention. It is to be understood that the following examples are not comprehensive or exhaustive of the many types of embodiments which can be prepared in accordance with the present invention.

Example 1

Coupling of Amines to EGAP (A) 1,3 Diaminopropane. 1,3 Diaminopropane (3.3 g) was mixed with 5 mL of deionized water. After the pH was adjusted to 8.2 with concentrated HCL, the solution was mixed with a solution of 0.5 g of 4-nitrophenyl chloroformate activated Pluronic™ F108 in 5.0 mL of deionized water. The reaction mixture, which immediately turned yellow, was kept at 25 C for 15 h. This solution was transferred to a dialysis tubing (with a molecular weight cutoff of 3500) and was dialyzed against 4 L of deionized water. During the 48 h dialysis process, water was changed five times until the low molecular weight material was assumed to be completely removed. The product was then recovered by lyophilization. The degree of substitution was determined by elemental nitrogen analysis. In this calculation the nitrogen content determined per a given mass of product was taken to exclusively derive from the attached diamine.

(B) 2-Aminoethanesulfonic Acid (Taurine). Taurine (3.4 g) was dissolved in 7 mL of deionized water, and the pH solution was adjusted to 9.4 with 2M Hcl. The solution was mixed with a 5 mL water solution of 0.5 g of 4-nitrophenyl chloroformate activated Pluronic™ F108. The resulting reaction mixture was kept at 25 C overnight, and the product was obtained after dialysis and lyophilization as described previously. The degree of substitution was determined through sulfur and nitrogen analysis of a known amount of product; its molar taurine content was then readily calculated.

(C) Glycyltryptophan (Gly-Trp). Two 11 mg portions of Gly-Trp were each dissolved in a vial with 2 mL of methanol. One of the vials contained 0.05 mL of 1.2 M TEA. To both vials was added 11 mg of 4-nitrophenyl chloroformate activated Pluronic™ F108, and the final solutions were kept at 25 C overnight. The reaction mixtures were then passed through PD-10 Sephadex G-25 columns, and the void fractions were pooled. The amount of bound Gly-Trp was determined by dry weight determination and photometric analysis using a molar extinction coefficient of 6170 $cm^{-1}$ $M^{-1}$ for the tryptophan residue.

Example 2

Calorimetric Observations of Fibronectin Conjugated to EGAP

PS latex particles with a diameter of 261 nm were purchased as a 10% (w/v) suspension were purchased from Seradyn, [State]. The block copolymer surfactant surfactant used was F108 having a molecular weight of 14600 were donated by BASF COW'S., [state]. Nsuccinimidyl-3-(2-pyridyldithiol) propionate (SPDP) was obtained from Pierce, [state]. Diihiothreitol (DTT) was from Bio-Rad, [state]. Fibronectin solution (FN, 1.5 mg/ml) was isolated from human plasma, and disposable prepacked PD-10 columns were purchased from Pharmacia, Wis.

The Pluronic™ F108-2-pyridyl disulfide derivative (GAP) was synthesized as described above.

Adsorption reaction was carried out in a mixture consisting of 10 µL of the suspension of PS latex particles and 200 µL of 0.5% (w/w) EGAP dissolved in deionized water. This mixture was incubated for 2 hours with shaking at room PS microspheres were washed and recovered by table centrifugation Eppendorf 5415C).

Thiolation of biomolecules the methodology described previously (4). Briefly, the reaction mixture of 2 mL of fibronectin solution and 20 pL of 5 mM SPDP solution was kept for 1 hour at room temperature with shaking, after which it was passed through a PD-10 column. Ile SPDP-modified fibronectin (FN-SPDP) was collected; its emergence from the PD-10 column was monitored by UV adsorbance at 280 nm. Thiolated fibronectin was then obtained by adding 4 liL of a 50 mM D7r solution to the SPDP-modified fibronectin and keeping the mixture for 30 minutes at room temperature. The sulfbydryl concentration was calculated by quantifying the concentration of released 2-thiopyridone as described earlier.

Low molecular weight reaction products were removed by passing the thiolated fibronectin (FN-SH) reaction mix through a PD-10 column. The coated PS latex particles were added to FN-SH or FN solution and the linking reaction was allowed to take place for 1 hour at room temperature under shaking. The latex particles were washed and characterized by means of differential scanning microcalorimetry (DSC). Quantification of the amount of FN or FN-SH bound onto the latex particles was performed by amino acid analysis as well as by Micro BCA assay, as described before. DSC (Hart Scientific, Model 4207) studies were carried out as reported previously.

Figure 3:
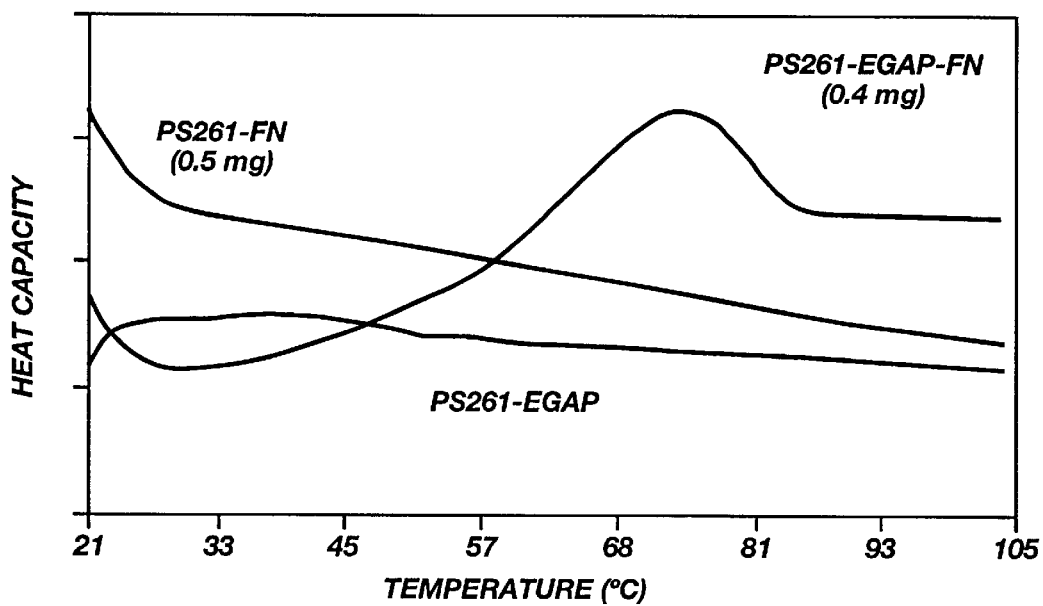
FIG. 3 is a graph illustrating the thermal stability of fibronectin (FN) adsorbed by a hydrophobic surface (PS261-FN), and conjugated to EGAP coated hydrophobic surface (PS261-EGAP-FN). Unconjugated EGAP adsorbed by a hydrophobic surface (PS261-EGAP) was used as a control.

FN shows melting transitions at different temperatures and with different enthalpic contents. It is therefore likely that surface adsorption might strongly affect the FN structure. FIG. 3 is a comparison of FN adsorbed and bound through the PEO tether offered by the modified Pluronic™ F108, respectively. No cooperative transitions are in evidence for the adsorbed protein, while FN tethered to the surface shows the normal, complex transition pattern. Apparent transition enthalpies for free and immobilized FN are listed in Table 1.

TABLE 1

| Fibronectin | $T_m$ (° C.) | $\Delta H$(K cal/mol) |
| --- | --- | --- |
| In PBS | 55–80 | 570 |
| Conjugated to EGAP | 55–80 | 440 |

Example 3

Calorimetric Observations of Human Serum Albumin Conjugated to EGAP

Human Serum Albumin (HSA) conjugated EGAP was thiolated, purified, and conjugated to EGAP essentially as described in Example 2. The attachment of HSA to a PEO tether, already in place at the surface, was an obvious route to retention of structure, as seen in FIG. 4. The three traces in the FIG. 4 represent the thermograms for protein in solution, protein adsorbed onto bare PS particles, and proteins attached to the surface through the Pluronic™ F108 intermediate. As with fibronectin, all cooperative transitions are absent from the protein-particle adsorption complex. However, the PEO-tethered sample shows the characteristic complex melting curve of native HSA, reflecting the differential collapse of the three lobes of this protein. The transition enthalpies associated with thermal unfolding of HSA in the three different states are listed in Table 2. Due to the irreversible nature of these thermal transitions it should be noted that the listed values represent apparent enthalpies.

TABLE 2

| Human Serum Albumin | $T_m$ (° C.) | $\Delta H$(K cal/mol) |
| --- | --- | --- |
| In PBS | 60–75 | 580 |
| Conjugated to EGAP | 60–75 | 460 |

Example 4

Cells Do Not Adhere to Hydrophobic Surface Coated with Block Copolymer Surfactants Osteoblast cells were seeded onto a polystyrene substrate which had been treated with C F108 or only in a localized circular area in the center of the substrate. As illustrated in FIG. 8, cells which were seeded in serum containing media did not attach to the PEO modified area but were found to attach, spread, and proliferate well on unmodified areas. FIG. 8a is a close-up displaying cells aligned at an interface between PEO treated and unmodified areas. In FIG. 8b, cells were fixed and removed from culture well after adequate time to lay down a substantial ECM. A dark spot in the center corresponds to the PEO treated area where there were no cells.

Example 5

EGAP is Not Toxic to Primary Breast Epithelial Cells

Surgical discard from reduction mammoplasty was digested by standard method into single and small cell aggregates of epithelial cells. Cells were placed on a Pluronic™ coated tissue culture plastic in CDM# media. Following a two week incubation at 37° C., 95% of cells were alive as indicated by the vital dyes.

Example 6

NIH 3T3 Cells Attach to and Grow on RGDS Conjugated EGAP

NIH 3T3 cells were attached to and grown on GRGDS conjugated EGAP as follows. EGAP formation and GRGDS conjugation was carried out essentially as described above. Briefly, the hydroxyl ends of Block copolymer surfactant was activated to form an EGAP using 4-nitrophenyl chloroformate followed by 2-pyridyl disulfide.

A portion of the EGAP was derivatized with the Bolton-Hunter Reagent. This allows the polymer to be labeled with radioactive iodine and thus provides a means to accurately determine the surface concentration of the EGAP.

GRGDS peptide was synthesized with a tyrosine residue at its carboxyl terminus using methods well known in the art. The tyrosine residue allows incorporation of radioactive iodine and thereby enables accurate determination of surface peptide concentration.

ESCA analyses of PS modified with F108 demonstrate that a high degree of PEO coverage is obtained. As illustrated in Table 3 below, this result has been confirmed by contact angle measurements which show that a substantial increase in the degree of substrate hydrophilicity occurs upon coating PS with F108.

TABLE 3

| Substrate | Average Contact Angle |
| --- | --- |
| Untreated Polystyrene | 82 |
| F-108 Coated Polystyrene | 68 |

The plateau concentration of F-108 adsorbed onto PS was determined by isotope $^{125}$I labeling and was found to be 3.3 mg/m$^2$. This corresponds to one triblock every 7.4 nm$^2$. ESCA measurements have also been used to confirm the presence of active sites for peptide coupling on PS coated with derivatized triblocks and the presence of peptides on PS conjugated with peptide via activated triblocks (Table 4).

TABLE 4

| Substrate | Treatment | Element | Atom % |
| --- | --- | --- | --- |
| F108-PS | Rxn w/AgNO$_3$ | Ag | 0.2 |
| PDS-F108-PS | Rxn w/AgNO$_3$ | Ag | 0.8 |
| PDS-F108-PS |  | N | 0.3 |
| PDC-F108-PS | Rxn w/GRGDS | N | 0.8 |

As a further means for characterizing PEO and GRGDS modified PS substrates, cell cultures were grown on conjugated EGAP coated culture surfaces. NIH 3T3 fibroblasts were seeded onto GRGDS conjugated EGAP coated polystyrene (RGD-PS), EGAP coated polystyrene (PDS-F108-PS), and F108 coated polystyrene (F108-PS) substrates at approximately 1×10$^4$/cm$^2$. Thirty minutes after seeding, the substrates were gently washed. The attached cells were incubated for 24 hours, after which, the substrates were again gently washed and fixed for counting. As illustrated in FIG. 9, RGD-PS were found to support cell adhesion, PDSF108-PS displayed an intermediate level of adhesiveness, and F108 coated polystyrene was relatively non-adhesive to fibroblast cells.

Example 7

NIH 3 T3 Cells Attach to GRGDSY Conjugated EGAP

Fibronectin peptide Gly-Arg-Gly-Asp-Ser-Tyr or GRGDSY was conjugated to activated F108 (EGAP) and used to coat polystyrene (PS) culture dishes as described above. Cells were seeded at 6×103 cells/cm$^2$ in DMEM supplemented with 10% bovine serum. Substrates were washed after 24 hrs. The attachment of NIT 3T3 cells to GRGDSY conjugated F108 (PDSF108/RGD) was compared with untreated PS surface (PS), PS surface coated with F108 alone (F108), F108 adsorbed PS treated with GRGDSY (not conjugated) (F108/RGD), and pyridyl disulfate activated F108 (EGAP) adsorbed PS without GRGDSY (PDSF108).

The results of NIH 3T3 attachment to these various surfaces is summarized below.

TABLE 5

| Substrate | Cell/cm$^2$ | Standard Dev. of Mean |
| --- | --- | --- |
| F108 | 0 | 0 |
| F108/RGD | 13 | 9.6 |
| PDSF108 | 462 | 38.5 |
| PDSF108/RGD | 5331 | 465.4 |
| PS | 5821 | 325.0 |

FIGS. 5 and 6, respectively, illustrate that NIH 3T3 cells do adhere and spread processes on GRGDSY conjugated EGAP surfaces, but do not adhere to F108 treated surface.

What is claimed and desired to be secured by United States Letters Patent is:

1. A method for modifying a hydrophobic surface to create adhesive and non-adhesive regions comprising the steps of:
   contacting a first region of the hydrophobic surface with a modified PPO- and PEO-containing triblock or diblock copolymer comprising an activated end group such that said modified copolymer adsorbs onto said first region, thereby converting said first region into a modified copolymer-coated region;
   contacting a second region of the hydrophobic surface with an unmodified PPO- and PEO-containing triblock or diblock copolymer such that said unmodified copolymer adsorbs onto said second region, thereby converting said second region into an unmodified copolymer-coated region; and
   conjugating a natural or recombinant biomolecule to the activated end group of the modified copolymer-coated region to convert said modified copolymer-coated region into a biomolecule-conjugated copolymer-coated region,
   wherein said biomolecule-conjugated copolymer-coated region is characterized by being adhesive to cells, viruses, and biomolecules and said unmodified copolymer-coated regions are characterized by being non-adhesive to cells, viruses, and biomolecules.

2. A method as in claim 1 wherein the biomolecule is selected from the group consisting of natural or recombinant proteins, enzymes, peptides, amino acids, and nucleic acids.

3. The method according to claim 1 wherein the biomolecule is selected from the group consisting of natural or recombinant extracellular matrix proteins, adhesive proteins, and combinations thereof.

4. The method according to claim 1 wherein the biomolecule is selected from the group consisting of natural or recombinant growth factors, mitogens, cytokines, growth peptides, differentiating factors and all combinations thereof.

5. The method according to claim 1 wherein the biomolecule is selected from the group consisting of natural or synthetic sugars, carbohydrates, polysaccharides and combinations thereof.

6. The method according to claim 1 wherein the biomolecule is selected from the group consisting of natural or synthetic lipids, sterols, fatty acids and combinations thereof.

7. The method according to claim 1 wherein the biomolecule is selected from the group consisting of natural or synthetic antibodies, antibody fragments, receptors, fragments of receptors, transmembrane proteins, fragments of transmembrane proteins and combinations thereof.

8. The method according to claim 1 wherein the copolymer is represented by the formula:

$$(HO-PEO)_c(HO-PEO)_d(PPO)_b$$

where (b) is an integer from 1 to 3, (c+d) is an integer between 0 and 5, and d is at least 1, where PEG is of the formula:

$$-(-C_2H_4-O-)_u-$$

where (u) is greater than 50, where PPO is of the formula $$-(C_3H_6-O-)_v-$$

where (v) is greater than 25.

9. The method according to claim 1 wherein the step of contacting a region of the hydrophobic surface with an unmodified PPO- and PEO-containing triblock or diblock copolymer is performed before the step of contacting a region of the hydrophobic surface with a modified PPO- and PEO-containing triblock or diblock copolymer comprising an activated end group.

10. A method for modifying a hydrophobic surface to create adhesive and non-adhesive regions comprising the steps of:
    conjugating a natural or recombinant biomolecule to an activated end group of a PEO- and PPO-containing triblock and diblock copolymer to form a biomolecule-conjugated copolymer;
    contacting a first region of the hydrophobic surface with the biomolecule-conjugated copolymer such that the biomolecule-conjugated copolymer adsorbs onto said first region, thereby converting said first region into a biomolecule-conjugated copolymer-coated region;
    contacting a second region of the hydrophobic surface with an unmodified PPO- and PEO-containing triblock or diblock copolymer such that said unmodified copolymer adsorbs onto said second region, thereby converting said second region into an unmodified copolymer-coated region; and
    wherein said biomolecule-conjugated copolymer-coated region is characterized by being adhesive to cells, viruses, and biomolecules and said unmodified copolymer-coated regions are characterized by being non-adhesive to cells, viruses, and biomolecules.

11. A method as in claim 10 wherein the biomolecule is selected from the group consisting of natural or recombinant proteins, enzymes, peptides, amino acids, and nucleic acids.

12. The method according to claim 10 wherein the biomolecule is selected from the group consisting of natural or recombinant extracellular matrix proteins, adhesive proteins, and combinations thereof.

13. The method according to claim 10 wherein the biomolecule is selected from the group consisting of natural or recombinant growth factors, mitogens, cytokines, growth peptides, differentiating factors and all combinations thereof.

14. The method according to claim 10 wherein the biomolecule is selected from the group consisting of natural or synthetic sugars, carbohydrates, polysaccharides and combinations thereof.

15. The method according to claim 10 wherein the biomolecule is selected from the group consisting of natural or synthetic lipids, sterols, fatty acids and combinations thereof.

16. The method according to claim 10 wherein the biomolecule is selected from the group consisting of natural or synthetic antibodies, antibody fragments, receptors, fragments of receptors, transmembrane proteins, fragments of transmembrane proteins and combinations thereof.

17. The method according to claim 10 wherein the copolymer is represented by the formula:

$$(HO-PEO)_c(HO-PEO)_d(PPO)_b$$

where (b) is an integer from 1 to 3, (c+d) is an integer between 0 and 5, and d is at least 1, where PEO is of the formula:

$$-(-C_2H_4-O-)_u-$$

where (u) is greater than 50, where PPO is of the formula $$-(-C_3H_6-O-)_v-$$

where (v) is greater than 25.

18. The method according to claim 10 wherein the step of contacting a region of the hydrophobic surface with an unmodified PPO- and PEO-containing triblock or diblock copolymer is performed before the step of contacting a region of the hydrophobic surface with a modified PPO- and PEO-containing triblock or diblock copolymer comprising an activated end group.

19. A device with adhesive and non-adhesive regions comprising:
    a hydrophobic surface partitioned into a first region and a second region;
    a PPO- and PEO-containing diblock or triblock copolymer absorbed onto said first region of said surface;
    a PPO- and PEO-containing diblock or triblock copolymer comprising an activated end group absorbed onto said second region; and
    a natural or recombinant biomolecule conjugated to said activated end group.

20. A device as in claim 19 wherein the biomolecule is selected from the group consisting of natural or recombinant growth factors, mitogens, growth peptides, differentiating factors, sugars, carbohydrates, polysaccharides, lipids, sterols, fatty acids, antibodies, antibody fragments, receptors, receptor fragments, transmembrane proteins, fragments of transmembrane proteins, and combinations thereof.

21. A device as in claim 19 wherein diblock or triblock copolymer is represented by the formula:

$$(HO-PEO)_c(HO-PEO)_d(PPO)_b$$

where (b) is an integer from 1 to 3, (c+d) is an integer between 0 and 5, and d is at least 1, where PEO is of the formula:

$$-(-C_2H_4-O-)_u-$$

where (u) is greater than 50, where PPO is of the formula $$-(C_3H_6-O-)_v-$$

where (v) is greater than 25.

* * * * *

UNITED STATES PATENT AND TRADEMARK OFFICE
CERTIFICATE OF CORRECTION

PATENT NO. : 6,670,199 B2
DATED : December 30, 2003
INVENTOR(S) : Karin Caldwell et al.

It is certified that error appears in the above-identified patent and that said Letters Patent is hereby corrected as shown below:

Column 19,
Line 10, please delete "(GAP)" and replace with -- (EGAP) --.

Column 23,
Line 4, please delete "PEG" and replace with -- PEO --.

Signed and Sealed this

Third Day of August, 2004

JON W. DUDAS
*Acting Director of the United States Patent and Trademark Office*